United States Patent
Stoessel et al.

(10) Patent No.: US 10,103,340 B2
(45) Date of Patent: Oct. 16, 2018

(54) METAL COMPLEXES

(75) Inventors: Philipp Stoessel, Frankfurt am Main (DE); Esther Breuning, Ober-Ramstadt (DE)

(73) Assignee: Merck Patent GmbH (DE)

( * ) Notice: Subject to any disclaimer, the term of this patent is extended or adjusted under 35 U.S.C. 154(b) by 1197 days.

(21) Appl. No.: 14/122,844

(22) PCT Filed: May 10, 2012

(86) PCT No.: PCT/EP2012/002013
§ 371 (c)(1),
(2), (4) Date: Nov. 27, 2013

(87) PCT Pub. No.: WO2012/163471
PCT Pub. Date: Dec. 6, 2012

(65) Prior Publication Data
US 2014/0091265 A1 Apr. 3, 2014

(30) Foreign Application Priority Data
Jun. 3, 2011 (EP) .................... 11004545

(51) Int. Cl.
| | |
|---|---|
| *H01L 51/54* | (2006.01) |
| *C09K 11/06* | (2006.01) |
| *H01L 51/00* | (2006.01) |
| *H05B 33/14* | (2006.01) |
| *C07F 15/00* | (2006.01) |
| *C07F 1/12* | (2006.01) |
| *H01L 51/50* | (2006.01) |

(52) U.S. Cl.
CPC ............ *H01L 51/0087* (2013.01); *C07F 1/12* (2013.01); *C07F 15/0033* (2013.01); *C07F 15/0086* (2013.01); *C09K 11/06* (2013.01); *H05B 33/14* (2013.01); *C09K 2211/1007* (2013.01); *C09K 2211/1011* (2013.01); *C09K 2211/1029* (2013.01); *C09K 2211/1044* (2013.01); *C09K 2211/1092* (2013.01); *C09K 2211/185* (2013.01); *H01L 51/0067* (2013.01); *H01L 51/0072* (2013.01); *H01L 51/5016* (2013.01); *H01L 2251/5384* (2013.01); *Y02E 10/549* (2013.01)

(58) Field of Classification Search
None
See application file for complete search history.

(56) References Cited

U.S. PATENT DOCUMENTS

| | | | |
|---|---|---|---|
| 7,442,797 B2 | 10/2008 | Itoh et al. | |
| 9,312,505 B2 * | 4/2016 | Brooks et al. ...... | C07F 15/0086 |
| 2006/0134461 A1 * | 6/2006 | Huo et al. ........... | C07F 15/0086 |
| | | | 428/690 |
| 2008/0036373 A1 | 2/2008 | Itoh et al. | |

FOREIGN PATENT DOCUMENTS

| | | |
|---|---|---|
| EP | 1683804 A2 | 7/2006 |
| EP | 2113548 A1 | 11/2009 |
| JP | 2008-037848 A | 2/2008 |
| WO | WO-2005/042444 A2 | 5/2005 |

OTHER PUBLICATIONS

Kuratsu, Masato, et al., "Magnetic Interaction of Tri- and Di-Oxytriphenylamine Radical Cation FeCl₄ Salts", Inorg. Chem., vol. 46, (2007), pp. 10153-10157.
International Search Report for PCT/EP2012/002013 dated Sep. 19, 2012.

* cited by examiner

*Primary Examiner* — Marie R. Yamnitzky
(74) *Attorney, Agent, or Firm* — Drinker Biddle & Reath LLP

(57) ABSTRACT

The present invention relates to a compound of the formula (1),

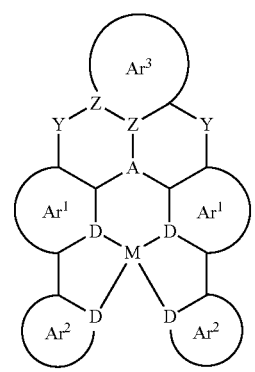

formula (1)

a process to prepare the compound of formula (1), a formulation containing the compound of formula (1) and an electronic device containing the compound of formula (1).

20 Claims, No Drawings

METAL COMPLEXES

CROSS-REFERENCE TO RELATED APPLICATIONS

This application is a national stage application (under 35 U.S.C. § 371) of PCT/EP2012/002013, filed May 10, 2012, which claims benefit of European application 11004545.7, filed Jun. 3, 2011.

The present invention relates to metal complexes which are suitable for use as emitters in organic electroluminescent devices.

The structure of organic electroluminescent devices (OLEDs) in which organic semiconductors are employed as functional materials is described, for example, in U.S. Pat. Nos. 4,539,507, 5,151,629, EP 0676461 and WO 98/27136. The emitting materials employed are frequently organometallic complexes which exhibit phosphorescence instead of fluorescence (M. A. Baldo et al., *Appl. Phys. Lett.* 1999, 75, 4-6). For quantum-mechanical reasons, an up to four-fold energy and power efficiency is possible using organometallic compounds as phosphorescence emitters. In general, there is still a need for improvement in the case of OLEDs which exhibit triplet emission, in particular with respect to efficiency, operating voltage and lifetime.

In accordance with the prior art, iridium or platinum complexes, in particular, are employed as triplet emitters in phosphorescent OLEDs. An improvement in the platinum complexes used can be achieved by employing metal complexes with tetradentate ligands, as a result of which the complexes have higher thermal stability (WO 2004/108857, WO 2005/042550, WO 2005/042444). However, there continues to be a need for improvement in the case of platinum complexes, in particular with respect to the thermal stability, the efficiency, the lifetime and/or the operating voltage.

The object of the present invention is therefore the provision of novel metal complexes which are suitable as emitters for use in OLEDs.

Surprisingly, it has been found that certain metal chelate complexes described in greater detail below achieve this object and result in improvements in the organic electroluminescent device. Furthermore, these metal complexes have high thermal stability. The present invention therefore relates to these metal complexes and to organic electroluminescent devices which comprise these complexes.

The invention relates to a compound of the formula (1),

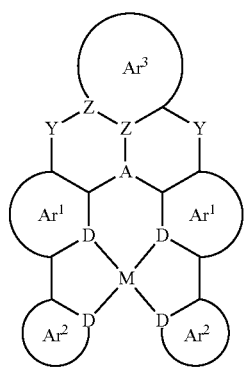

formula (1)

where the following applies to the symbols used:
M is a transition metal;
A is N, P, B, C⁻ or CR;
Y is on each occurrence, identically or differently, $CR_2$, NR, O, S or a single bond, where a maximum of one group Y stands for a single bond;
Z is on each occurrence, identically or differently, C or N, with the proviso that both Z stand for C if $Ar^3$ stands formula an aromatic or heteroaromatic six-membered ring, and that either both Z stand for C or one Z stands for C and the other Z stands for N if $Ar^3$ stands for a heteroaromatic five-membered ring;
D is on each occurrence, identically or differently, C or N;
$Ar^1$ is on each occurrence, identically or differently, together with the group D and the three carbon atoms explicitly drawn in, an aryl or heteroaryl group having 5 to 13 aromatic ring atoms, preferably having 5 to 10 aromatic ring atoms, which may in each case be substituted by one or more radicals $R^1$;
$Ar^2$ is on each occurrence, identically or differently, together with the group D and the carbon atom explicitly drawn in, an aryl or heteroaryl group having 5 to 13 aromatic ring atoms, preferably having 5 to 10 aromatic ring atoms, which may in each case be substituted by one or more radicals $R^1$;
$Ar^3$ is, together with the two groups Z and the carbon atom drawn in, an aryl or heteroaryl group having 5 to 10 aromatic ring atoms, which may be substituted by one or more radicals $R^1$;
R, $R^1$ is on each occurrence, identically or differently, H, D, F, Cl, Br, I, $N(R^2)_2$, CN, $NO_2$, OH, COOH, C(=O)$N(R^2)_2$, $Si(R^2)_3$, $B(OR^2)_2$, C(=O)$R^2$, P(=O)$(R^2)_2$, S(=O)$R^2$, S(=O)$_2R^2$, $OSO_2R^2$, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which may be substituted by one or more radicals $R^2$, where one or more non-adjacent $CH_2$ groups may be replaced by $R^2C$=$CR^2$, C≡C, $Si(R^2)_2$, C=O, $NR^2$, O, S or $CONR^2$ and where one or more H atoms may be replaced by D, F, Cl, Br, I or CN, or an aromatic or heteroaromatic ring system having 5 to 60 aromatic ring atoms, which may in each case be substituted by one or more radicals $R^2$, or an aryloxy or heteroaryloxy group having 5 to 40 aromatic ring atoms, which may be substituted by one or more radicals $R^2$, or an aralkyl or heteroaralkyl group having 5 to 40 aromatic ring atoms, which may be substituted by one or more radicals $R^2$, or a diarylamino group, diheteroarylamino group or arylheteroarylamino group having 10 to 40 aromatic ring atoms, which may be substituted by one or more radicals $R^2$; two adjacent radicals R or two adjacent radicals $R^1$ here may also form a mono- or polycyclic, aliphatic or aromatic ring system with one another; furthermore, the radicals $R^1$ which are bonded to adjacent groups $Ar^1$ and $Ar^2$ may also form a mono- or polycyclic, aliphatic or aromatic ring system with one another;
$R^2$ is on each occurrence, identically or differently, H, D, F, Cl, Br, I, $N(R^3)_2$, CN, $NO_2$, $Si(R^3)_3$, $B(OR^3)_2$, C(=O)$R^3$, P(=O)$(R^3)_2$, S(=O)$R^3$, S(=O)$_2R^3$, $OSO_2R^3$, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which may be substituted by one or more radicals $R^3$, where one or more non-adjacent $CH_2$ groups may be replaced by $R^3C$=$CR^3$, C≡C, $Si(R^3)_2$, C=O, $NR^3$, O, S or $CONR^3$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^3$, or an aryloxy or heteroaryloxy group having 5 to 40 aromatic ring atoms, which may be substituted by one or more radicals $R^3$, or an aralkyl or heteroaralkyl group having 5 to 40 aromatic ring atoms, which may be substituted by one or more radicals $R^3$, or a diarylamino group, diheteroarylamino group or arylheteroarylamino group having 10 to 40 aromatic ring atoms, which may be substituted by one or more radicals $R^3$; two or more adjacent radicals $R^3$ here may form a mono- or polycyclic, aliphatic ring system with one another;

$R^3$ is on each occurrence, identically or differently, H, D, F or an aliphatic, aromatic and/or heteroaromatic hydrocarbon radical having 1 to 20 C atoms, in which, in addition, one or more H atoms may be replaced by F; two or more substituents $R^3$ here may also form a mono- or polycyclic, aliphatic ring system with one another.

In the definition of Z, "if $Ar^3$ stands for an aromatic or heteroaromatic six-membered ring" means that the part of the group $Ar^3$ which is bonded directly to A and the two groups Y is an aromatic or heteroaromatic six-membered ring. Correspondingly, in the definition of Z, "if $Ar^3$ stands for a heteroaromatic five-membered ring" means that the part of the group $Ar^3$ which is bonded directly to A and the two groups Y is a heteroaromatic five-membered ring. It is of course also possible for other aromatic or heteroaromatic groups to be condensed onto this six- or five-membered ring so that a larger condensed aromatic or heteroaromatic group forms. This is depicted diagrammatically below, where the bond to Y and to A is also depicted in each case:

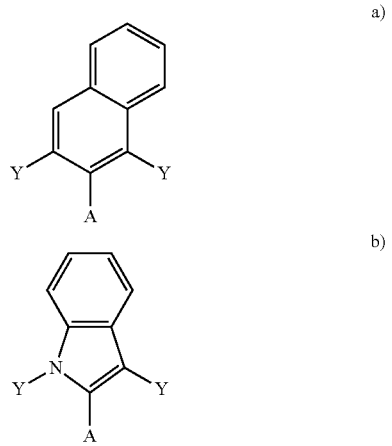

Thus, in the sense of the present invention, the structure depicted under a) is a structure in which $Ar^3$ stands for an aromatic six-membered ring and the structure depicted under b) is a structure in which $Ar^3$ stands for a heteroaromatic five-membered ring.

An aryl group in the sense of this invention contains 6 to 40 C atoms; a heteroaryl group in the sense of this invention contains 2 to 40 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, phenanthrene, quinoline, isoquinoline, etc.

An aromatic ring system in the sense of this invention contains 6 to 60 C atoms in the ring system. A heteroaromatic ring system in the sense of this invention contains 1 to 60 C atoms and at least one heteroatom in the ring system, with the proviso that the sum of C atoms and heteroatoms is at least 5. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be interrupted by a non-aromatic unit (preferably less than 10% of the atoms other than H), such as, for example, a C, N or O atom or a carbonyl group. Thus, for example, systems such as 9,9'-spirobifluorene, 9,9-diarylfluorene, triarylamine, diaryl ether, stilbene, etc., are also intended to be taken to be aromatic ring systems in the sense of this invention, as are systems in which two or more aryl groups are interrupted, for example, by a linear or cyclic alkyl group or by a silyl group. Furthermore, systems in which two or more aryl or heteroaryl groups are bonded directly to one another, such as, for example, biphenyl or terphenyl, are likewise intended to be taken to be an aromatic or heteroaromatic ring system.

A cyclic alkyl, alkoxy or thioalkoxy group in the sense of this invention is taken to mean a monocyclic, bicyclic or polycyclic group.

For the purposes of the present invention, a $C_1$- to $C_{40}$-alkyl group, in which, in addition, individual H atoms or $CH_2$ groups may be substituted by the above-mentioned groups, is taken to mean, for example, the radicals methyl, ethyl, n-propyl, i-propyl, cyclopropyl, n-butyl, i-butyl, s-butyl, t-butyl, cyclobutyl, 2-methylbutyl, n-pentyl, s-pentyl, tert-pentyl, 2-pentyl, neopentyl, cyclopentyl, n-hexyl, s-hexyl, tert-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, adamantyl, trifluoromethyl, pentafluoroethyl or 2,2,2-trifluoroethyl. An alkenyl group is taken to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is taken to mean, for example, ethynyl, propynyl, butynyl, pentynyl, hexynyl, heptynyl or octynyl. A $C_1$- to $C_{40}$-alkoxy group is taken to mean, for example, methoxy, trifluoromethoxy, ethoxy, n-propoxy, i-propoxy, n-butoxy, i-butoxy, s-butoxy, t-butoxy or 2-methylbutoxy.

An aromatic or heteroaromatic ring system having 5-60 aromatic ring atoms, which may also in each case be substituted by the radicals R mentioned above and which may be linked to the aromatic or heteroaromatic ring system via any desired positions, is taken to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, cis or trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

As stated above, adjacent radicals R or adjacent radicals $R^1$ or radicals $R^1$ on adjacent aryl or heteroaryl groups $Ar^1$ and $Ar^2$ may also form a ring system with one another. Adjacent radicals in the sense of the present invention are taken to mean radicals which are either bonded to the same atom, for example the radicals R if the group Y stands for $CR_2$, or radicals which are bonded to atoms which are bonded directly to one another. Adjacent aryl or heteroaryl groups $Ar^1$ and $Ar^2$ are taken to mean aryl or heteroaryl groups $Ar^1$ and $Ar^2$ which are bonded directly to one another. The radicals here are as defined above, and two radicals are bonded to one another in each case with formal removal of a hydrogen atom. If the radicals are alkyl groups, the formation of a condensed-on cycloalkyl group, for example, is thus possible. If the radicals are vinyl groups or one vinyl group and one hydrogen atom, the formation of a condensed aryl group, for example, is thus possible. If the radicals R or $R^1$ form a ring system, it is preferably a five-membered ring or a six-membered ring.

Preference is given to compounds of the formula (1), characterised in that they are uncharged, i.e. are electrically neutral. This is achieved in a simple manner by selecting the charge of the ligand in such a way that it compensates for the charge of the complexed metal atom M. The charge of the ligand arises from the number of coordinating carbon atoms, each of which have a negative charge, and, where appropriate, by the group A if this group stands for $C^-$.

Preference is furthermore given to compounds of the formula (1), characterised in that the sum of the valence electrons around the metal atom is 16.

The metal M is preferably selected from the group consisting of platinum, palladium, nickel, rhodium, iridium and gold. The above-mentioned metals are particularly preferably in the oxidation states Pt(II), Pd(II), Ni(II), Rh(I), Ir(I) and Au(III). Particular preference is given to Pt(II), Ir(I) and Au(III). Very particular preference is given to Pt(II).

Furthermore, two groups D in the compound according to the invention preferably stand for N, and the other two groups D stand for C. Particularly preferably, either both groups D in the groups $Ar^1$ stand for N and both groups D in the groups $Ar^2$ stand for C, or both groups D in the groups $Ar^1$ stand for C and both groups D in the groups $Ar^2$ stand for N.

Furthermore preferably, A stands for N or P, particularly preferably for N.

Particularly preferably, the above-mentioned preferences occur simultaneously and M is Pt(II), either both groups D in the groups $Ar^1$ stand for N and both groups D in the groups $Ar^2$ stand for C, or both groups D in the groups $Ar^1$ stand for C and both groups D in the groups $Ar^2$ stand for N and A stands for N.

Furthermore preferably, Y stands, identically or differently on each occurrence, for $CR_2$ or for a single bond, where a maximum of one group Y stands for a single bond. Particularly preferably, Y stands, identically or differently on each occurrence, for $CR_2$.

In a further preferred embodiment of the invention, both bridges Y are selected identically.

Preferred structures of the formula (1) are therefore the structures of the following formula (2),

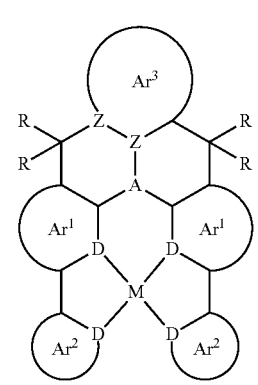

formula (2)

where the symbols used have the meanings given above.

In a preferred embodiment of the invention, $Ar^3$ is selected from the structures of the following formulae (3), (4) and (5),

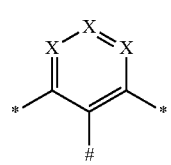

formula (3)

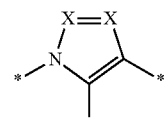

formula (4)

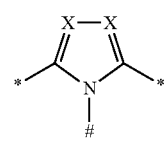

formula (5)

where X stands, identically or differently on each occurrence, for $CR^1$ or N or where two adjacent groups X in formula (3) together stand for NR, O or S and the other group X stands for $CR^1$ or N; * indicates the bond to Y and # indicates the bond to A. Particularly preferred groups $Ar^3$ are structures of the formula (3).

In a preferred embodiment of the structures of the formula (3) to (5), X stands, identically or differently on each occurrence, for $CR^1$.

The part-ligands $Ar^1$—$Ar^2$ are preferably bidentate monoanionic ligands which, with the transition metal M, contain a cyclometallated five-membered ring having at least one metal-carbon bond. These are, in particular, ligands as are generally used in the area of phosphorescent metal complexes for organic electroluminescent devices, i.e. ligands of the type phenylpyridine, naphthylpyridine, phenylquinoline, phenylisoquinoline, etc., each of which may be substituted by one or more radicals $R^1$. In each case one of the following groups (6) to (16) is preferably suitable as group $Ar^1$ and in each case one of the following groups (17) to (38) is preferably suitable as group $Ar^2$. The groups here are preferably selected in such a way that one of the groups $Ar^1$ and $Ar^2$ in the part-ligand $Ar^1$—$Ar^2$ is bonded via a neutral nitrogen atom or a carbene carbon atom and the other of the groups $Ar^1$ and $Ar^2$ in the part-ligand $Ar^1$—$Ar^2$ is bonded via a negatively charged carbon atom or a negatively charged nitrogen atom.

Suitable structures $Ar^1$ are thus the structures of the following formulae (6) to (16),

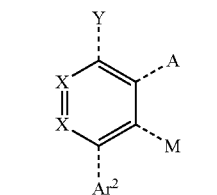

formula (6)

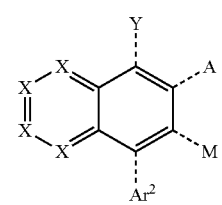

formula (7)

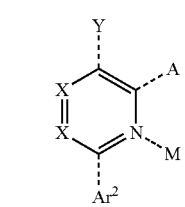

formula (8)

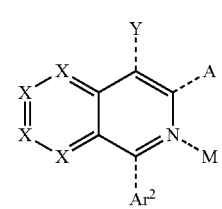

formula (9)

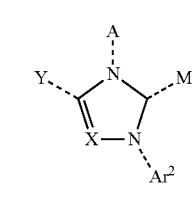

formula (10)

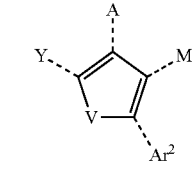

formula (11)

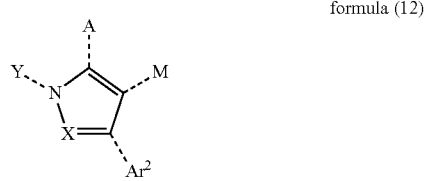

formula (12)

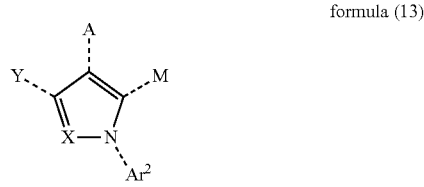

formula (13)

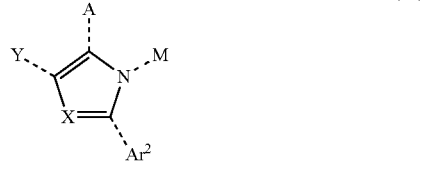

formula (14)

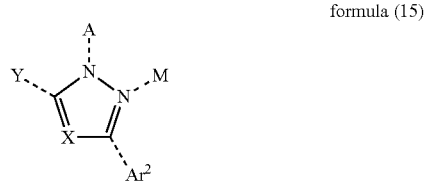

formula (15)

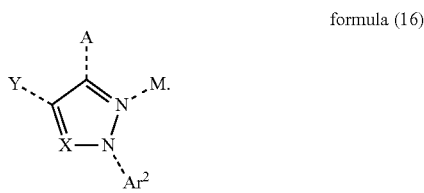

formula (16)

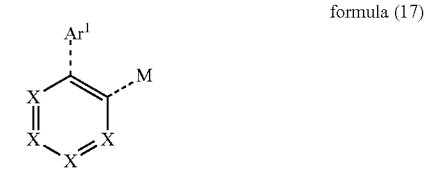

Suitable structures $Ar^2$ are the structures of the following formulae (17) to (38),

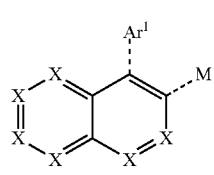

formula (17)

formula (18)

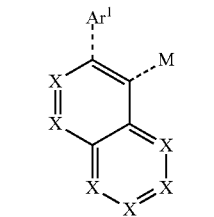

formula (19)

-continued
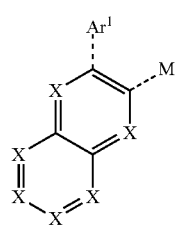
formula (20)
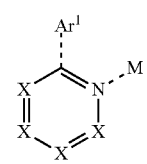
formula (21)
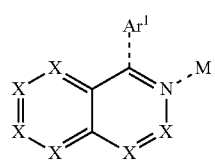
formula (22)
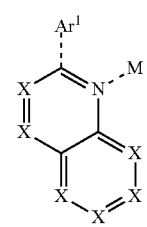
formula (23)
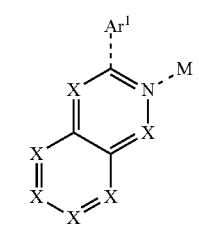
formula (24)
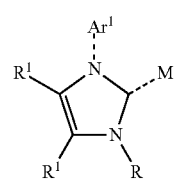
formula (25)
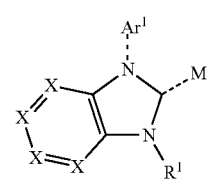
formula (26)
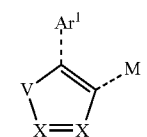
formula (27)
-continued
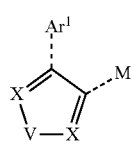
formula (28)
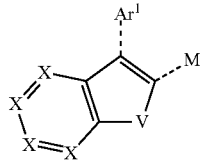
formula (29)
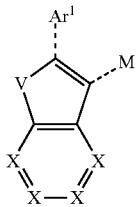
formula (30)
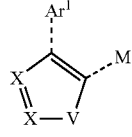
formula (31)
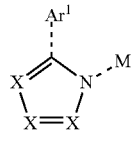
formula (32)
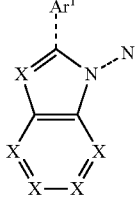
formula (33)
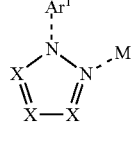
formula (34)
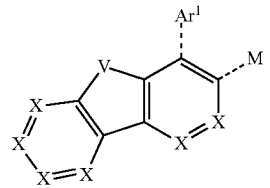
formula (35)

-continued

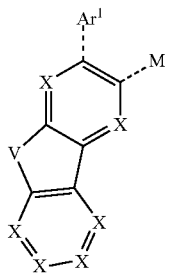
formula (36)

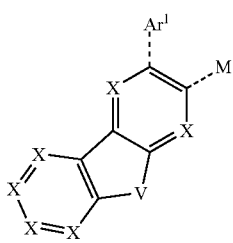
formula (37)

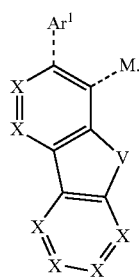
formula (38)

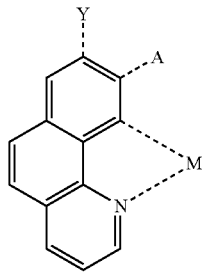

In the structures of the formulae (6) to (38), the bond to A, Y, M and Ar¹ or Ar² is in each case indicated by dashed bonds.

X in the formulae (6) to (38) stands on each occurrence, identically or differently, for $CR^1$ or N, V stands on each occurrence, identically or differently, for O, S or $NR^1$, and R has the same meaning as described above.

Preferably a maximum of three symbols X in each group stand for N, particularly preferably a maximum of two symbols X in each group stand for N, very particularly preferably a maximum of one symbol X in each group stands for N. Especially preferably all symbols X stand for $CR^1$.

As stated above, two radicals on adjacent groups Ar¹ and Ar² may also form a ring with one another. A ring closure of this type preferably takes place via a group $CR^2=CR^2$ or via a group $CR^2=N$. This may also result in the formation of a new aryl or heteroaryl group, so that Ar¹ and Ar² no longer represent separate aryl groups. This is illustrated below for the example where Ar¹=phenyl and Ar²=pyridine, where a ring-closure reaction of this type results in the formation of a phenanthridine structure. Analogous ring-closure reactions are also possible with other groups Ar¹ and Ar².

Preferred radicals $R^1$ on Ar¹, Ar² or Ar³ are selected on each occurrence, identically or differently, from the group consisting of H, D, F, Br, I, $N(R^2)_2$, CN, $Si(R^2)_3$, $B(OR^2)_2$, $C(=O)R^2$, a straight-chain alkyl group having 1 to 10 C atoms or an alkenyl group having 2 to 10 C atoms or a branched or cyclic alkyl group having 3 to 10 C atoms, each of which may be substituted by one or more radicals $R^2$, where one or more H atoms may be replaced by D or F, or an aromatic or heteroaromatic ring system having 5 to 30 aromatic ring atoms, which may in each case be substituted by one or more radicals $R^2$; two adjacent radicals $R^1$ or two radicals $R^1$ on adjacent groups Ar¹ and Ar² here may also form a mono- or polycyclic, aliphatic ring system with one another. These radicals $R^1$ are particularly preferably selected on each occurrence, identically or differently, from the group consisting of H, D, F, $N(R^2)_2$, a straight-chain alkyl group having 1 to 6 C atoms or a branched or cyclic alkyl group having 3 to 10 C atoms, where one or more H atoms may be replaced by D or F, or an aromatic or heteroaromatic ring system having 5 to 24 aromatic ring atoms, which may in each case be substituted by one or more radicals $R^2$; two adjacent radicals R or R with $R^1$ here may also form a mono- or polycyclic, aliphatic ring system with one another.

If the group Y stands for a group NR, the group R then preferably stands, identically or differently on each occurrence, for an aromatic or heteroaromatic ring system having 5 to 18 aromatic ring atoms, which may in each case be substituted by one or more radicals $R^2$ and which preferably contains no condensed aryl or heteroaryl groups.

If the group Y stands for a group $CR_2$, the group R then preferably stands, identically or differently on each occurrence, for H, D, a straight-chain alkyl group having 1 to 10 C atoms or an alkenyl or alkynyl group having 2 to 10 C atoms or a branched or cyclic alkyl group having 3 to 10 C atoms, each of which may be substituted by one or more radicals $R^2$, where one or more H atoms may be replaced by D or F, or an aromatic or heteroaromatic ring system having 5 to 18 aromatic ring atoms, which may in each case be substituted by one or more radicals $R^2$ and which preferably contains no condensed aryl or heteroaryl groups; two or more radicals R which are bonded to the same carbon atom here may also form a mono- or polycyclic, aliphatic or aromatic ring system with one another. Particularly preferred radicals R are selected on each occurrence, identically or differently, from the group consisting of H, a straight-chain alkyl group having 1 to 5 C atoms, in particular methyl, or a branched or cyclic alkyl group having 3 to 5 C atoms, in particular isopropyl or tert-butyl, where one or more H atoms may be replaced by D or F, or an aromatic or heteroaromatic ring system having 5 to 12 aromatic ring atoms, which may in each case be substituted by one or more radicals $R^2$; two radicals R which are bonded to the same carbon atom here may also form a mono- or polycyclic, aliphatic or aromatic ring system with one another.

If the radicals R which are bonded to the same carbon atom form a ring system with one another, this is, in a preferred embodiment of the invention, a structure of the following formula (a), formula (b) or formula (c),

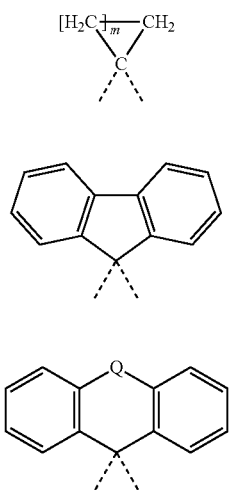

formula (a)

formula (b)

formula (c)

where Q stands for $C(R^2)_2$, $NR^2$, O or S, the structures may also be substituted by one or more radicals $R^2$ and m preferably stands for 1, 2, 3, 4 or 5, particularly preferably for 3 or 4. The bonds shown in dashed form here stand for the bond from the group to $Ar^1$ and $Ar^3$.

The above-mentioned preferred embodiments can be combined with one another as desired. In a particularly preferred embodiment of the invention, the above-mentioned preferred embodiments apply simultaneously.

In a preferred embodiment of the invention, the following therefore applies to the compounds of the formula (1):

M is selected from the group consisting of platinum, palladium, nickel, rhodium, iridium and gold, in particular Pt(II), Pd(II), Ni(II), Rh(I), Ir(I) and Au(III);

D is on each occurrence, identically or differently, C or N, where two groups D stand for N and the other two groups D stand for C;

A is N or P;

Y is, identically or differently on each occurrence, $CR_2$ or a single bond, where a maximum of one group Y stands for a single bond;

$Ar^3$ is selected from the above-mentioned structures of the formulae (3), (4) or (5);

$Ar^1$ is selected from the above-mentioned structures of the formulae (6) to (16);

$Ar^2$ is selected from the above-mentioned structures of the formulae (17) to (38);

$R^1$ is selected on each occurrence, identically or differently, from the group consisting of H, D, F, Br, I, $N(R^2)_2$, CN, $Si(R^2)_3$, $B(OR^2)_2$, $C(=O)R^2$, a straight-chain alkyl group having 1 to 10 C atoms or an alkenyl group having 2 to 10 C atoms or a branched or cyclic alkyl group having 3 to 10 C atoms, each of which may be substituted by one or more radicals $R^2$, where one or more H atoms may be replaced by D or F, or an aromatic or heteroaromatic ring system having 5 to 30 aromatic ring atoms, which may in each case be substituted by one or more radicals $R^2$; two adjacent radicals $R^1$ or two radicals $R^1$ on adjacent groups $Ar^1$ and $Ar^2$ here may also form a mono- or polycyclic, aliphatic ring system with one another;

R is, for Y=NR, identically or differently on each occurrence, an aromatic or heteroaromatic ring system having 5 to 18 aromatic ring atoms, which may in each case be substituted by one or more radicals $R^2$ and which preferably contains no condensed aryl or heteroaryl groups;

and is, for Y=$CR_2$, identically or differently, H, D, a straight-chain alkyl group having 1 to 10 C atoms or an alkenyl or alkynyl group having 2 to 10 C atoms or a branched or cyclic alkyl group having 3 to 10 C atoms, each of which may be substituted by one or more radicals $R^2$, where one or more H atoms may be replaced by D or F, or an aromatic or heteroaromatic ring system having 5 to 18 aromatic ring atoms, which may in each case be substituted by one or more radicals $R^2$ and which preferably contains no condensed aryl or heteroaryl groups; two or more radicals R which are bonded to the same carbon atom here may also form a mono- or polycyclic, aliphatic or aromatic ring system with one another.

In a particularly preferred embodiment of the invention, the following applies to the compounds of the formula (1) or formula (2):

M is selected from the group consisting of Pt(II), Ir(I) and Au(III), in particular Pt(II).

D is equal to N in both groups $Ar^1$ and is equal to C in both groups $Ar^2$ or is equal to C in both groups $Ar^1$ and is equal to N in both groups $Ar^2$;

A is N;

Y is on each occurrence $CR_2$, where the two groups Y are selected identically;

$Ar^3$ is selected from the above-mentioned structures of the formula (3);

$Ar^1$ is selected from the above-mentioned structures of the formulae (6) to (16);

$Ar^2$ is selected from the above-mentioned structures of the formulae (17) to (38);

$R^1$ is selected on each occurrence, identically or differently, from the group consisting of H, D, F, $N(R^2)_2$, a straight-chain alkyl group having 1 to 6 C atoms or a branched or cyclic alkyl group having 3 to 10 C atoms, where one or more H atoms may be replaced by D or F, or an aromatic or heteroaromatic ring system having 5 to 24 aromatic ring atoms, which may in each case be substituted by one or more radicals $R^2$; two adjacent radicals R or R with $R^1$ here may also form a mono- or polycyclic, aliphatic ring system with one another;

R is, for Y=NR, identically or differently on each occurrence, an aromatic or heteroaromatic ring system having 5 to 18 aromatic ring atoms, which may in each case be substituted by one or more radicals $R^2$ and which preferably contains no condensed aryl or heteroaryl groups;

and, for Y=$CR_2$, is selected, identically or differently, from the group consisting of H, a straight-chain alkyl group having 1 to 5 C atoms, in particular methyl, or a branched or cyclic alkyl group having 3 to 5 C atoms, in particular isopropyl or tert-butyl, where one or more H atoms may be replaced by D or F, or an aromatic or heteroaromatic ring system having 5 to 12 aromatic ring atoms, which may in each case be substituted by one or more radicals $R^2$; two radicals R which are bonded to the same carbon atom here may also form a mono- or polycyclic, aliphatic or aromatic ring system with one another.

The ligands of the compounds according to the invention can be prepared in accordance with Scheme 1.

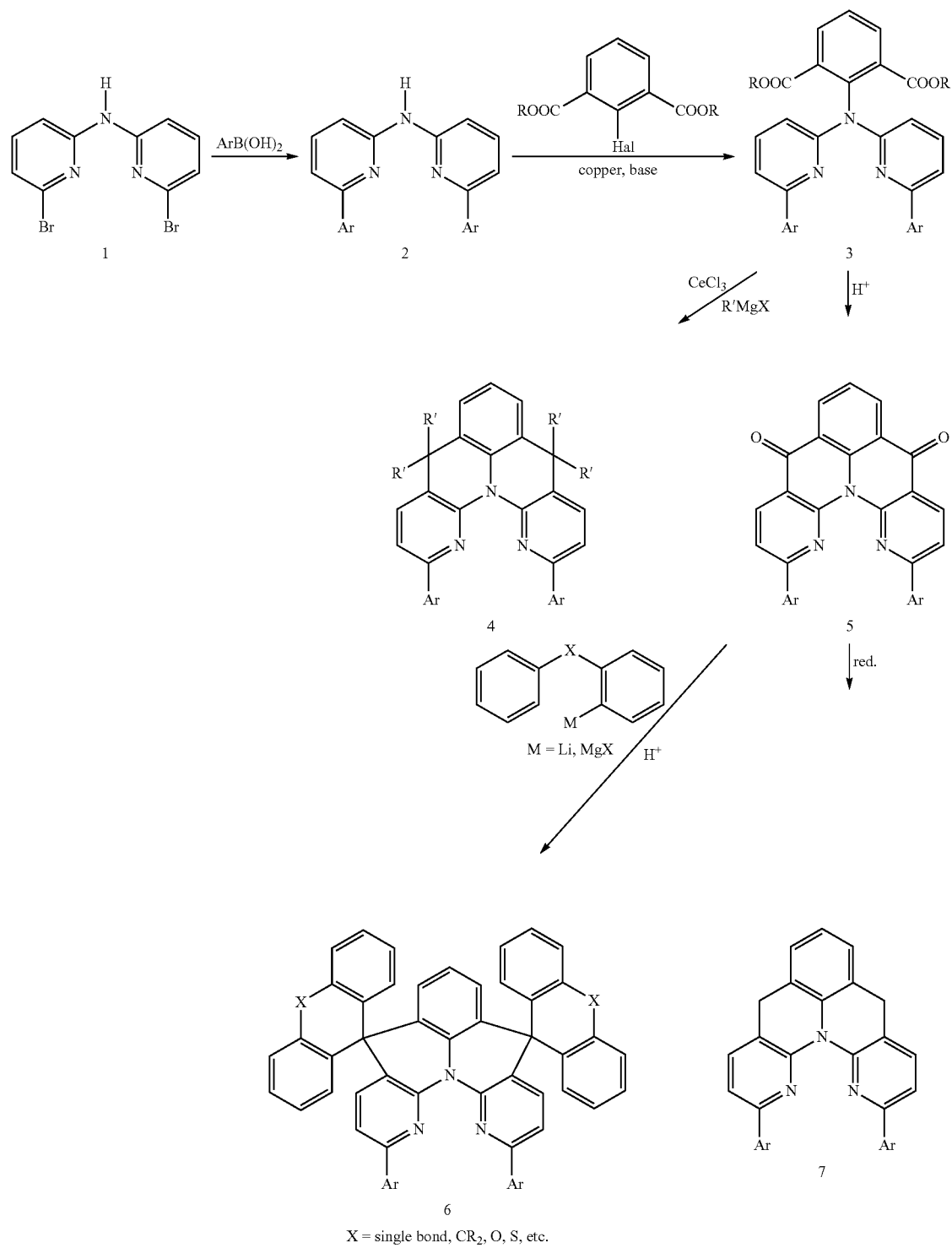

The dibromide 1 can be converted into 2 by Suzuki coupling. Reaction of 2 with 2-haloisophthalic acid esters via Ullmann coupling and subsequent acidic cyclisation results in the bisketone 5, which can be converted into the ligand 7 by reduction using hydrazine hydrate or BH$_3$×THF. An addition reaction of suitable aryllithium or arylmagnesium compounds and subsequent acidic cyclisation of the diol formed as intermediate results in ligands of type 6. Ligands of type 4 can be obtained from 3 by cerium-promoted Grignard addition and subsequent cyclisation of the diol formed as intermediate. These structures may of course also have further substituents. Further functionalisation of the ligands of type 4, 6 and 7 is possible in accordance with Scheme 2 via halogenation and C—C or C—N coupling.

Scheme 2
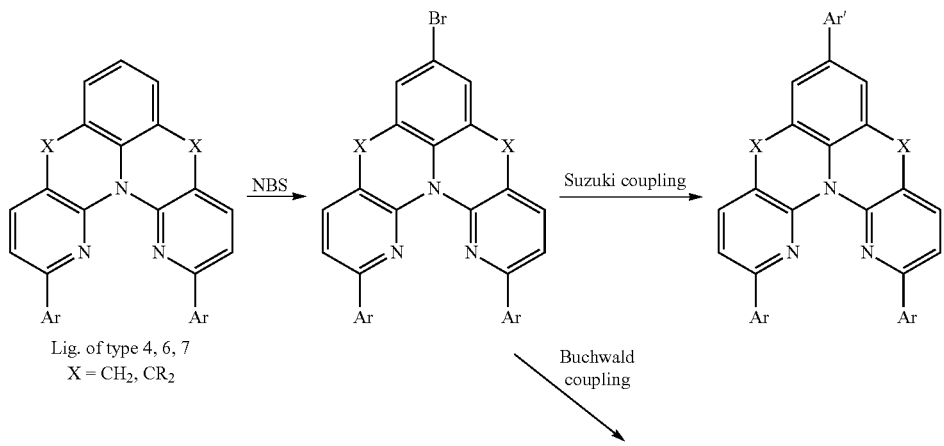
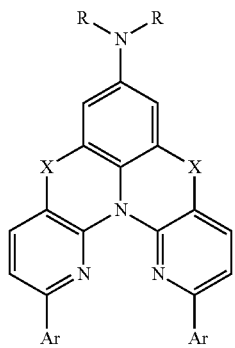
A further possibility of preparing ligands of type 15, 16 and 17 is shown in Scheme 3, where the synthetic procedure uses similar steps as shown in Scheme 1.
Scheme 3:
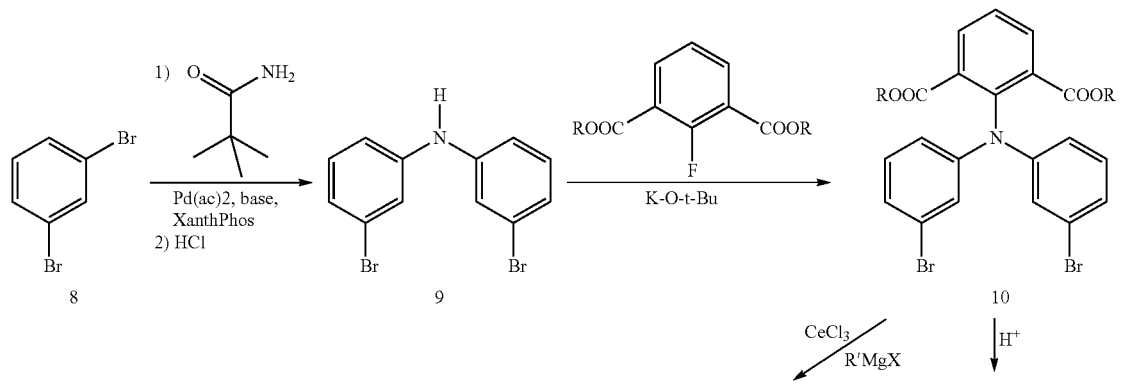

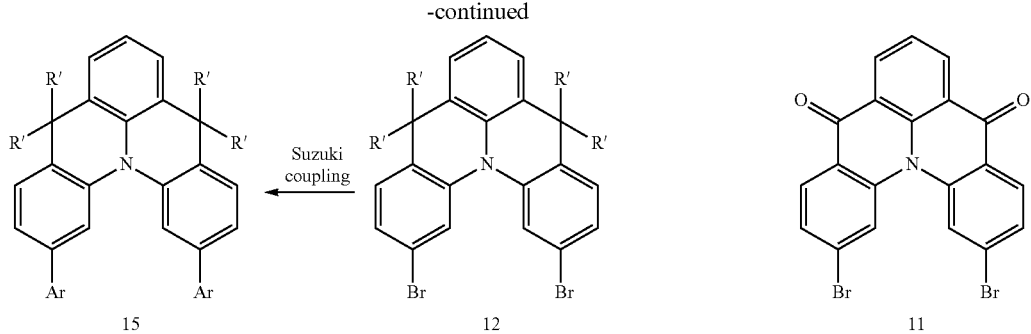
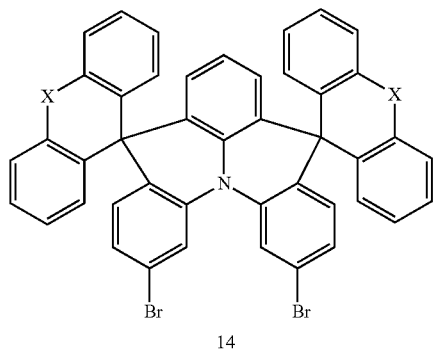
14
X = single bond, CR$_2$, O, S, etc.
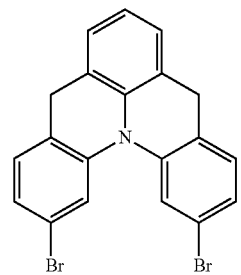
13
Suzuki coupling ↓    Suzuki coupling ↓
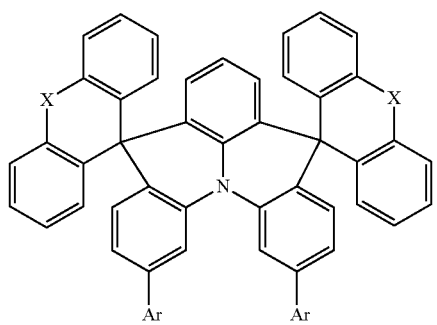
17
Ar = 2-N-heteroarylboronic acids, such as, e.g., 2-pyridineboronic acid
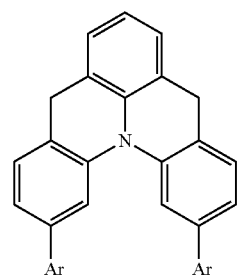
16

The complexing of the ligands of type 4, 6, 7, 15, 16 and 17 to give the complexes according to the invention can be carried out as shown in Scheme 4 for ligands of type 4, where other Pt precursors can also be used entirely analogously.

Scheme 4:

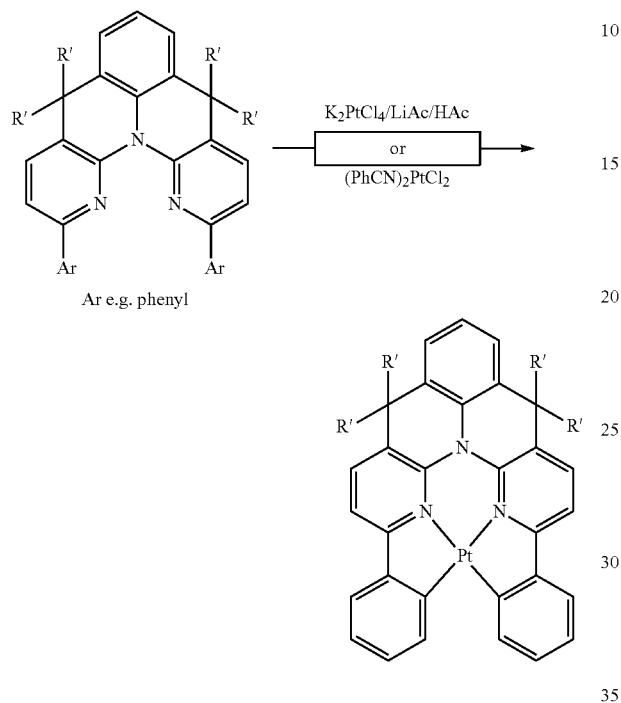

Ar e.g. phenyl

The metal complexes according to the invention can in principle be prepared by various processes in which the ligand is reacted with a suitable metal precursor. The present invention therefore furthermore relates to a process for the preparation of the compounds of the formula (1) by reaction of the corresponding free ligands with a suitable metal compound. Suitable platinum starting materials are, for example, $PtCl_2$, $K_2[PtCl_4]$, $PtCl_2(DMSO)_2$, $Pt(Me)_2(DMSO)_2$, $PtCl_2(benzonitrile)_2$, $PtCl_2(acetonitrile)_2$ or Pt-olefin complexes, such as, for example, $(COD)PtCl_2$. Suitable iridium starting materials are, for example, iridium(III) chloride hydrate, iridium-olefin complexes, for example with COD as ligand, $Ir(acac)_3$, $Ir(tBu-acac)_3$ or Vaska's complex. Suitable gold starting materials are, for example, $AuCl_3$ or $HAuCl_4$.

The synthesis can also be activated thermally, photochemically and/or by microwave radiation. In a possible embodiment of the invention, the reaction is carried out in the melt without the use of an additional solvent. "Melt" here means that the ligand is in molten form and the metal precursor is dissolved or suspended in this melt. In a further possible embodiment of the invention, the corresponding free ligand is reacted with the metal precursor, for example $K_2PtCl_4$, in glacial acetic acid.

These processes, optionally followed by purification, such as, for example, recrystallisation or sublimation, enable the compounds of the formula (1) according to the invention to be obtained in high purity, preferably greater than 99% (determined by means of $^1$H-NMR and/or HPLC).

Examples of suitable compounds according to the invention are the structures shown in the following table.

(1)

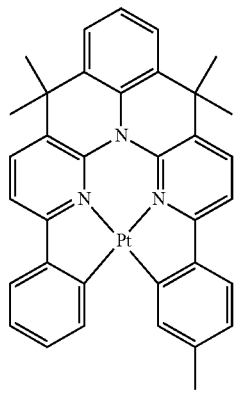

(2)

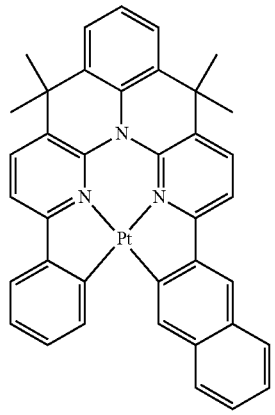

(3)

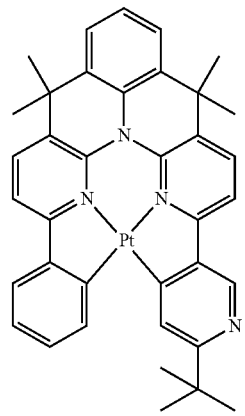

(4)

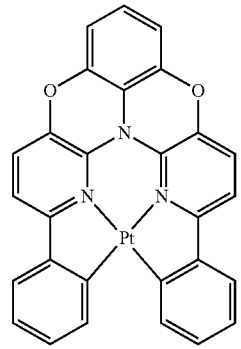

-continued
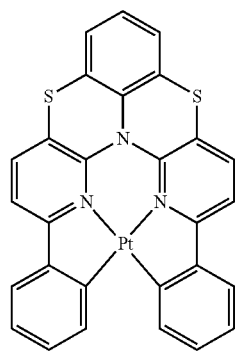
(5)
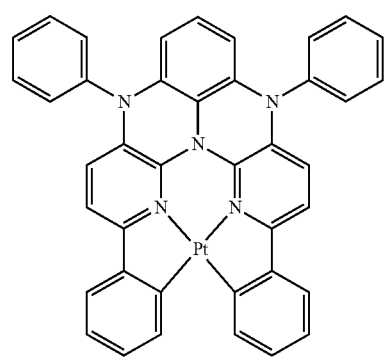
(6)
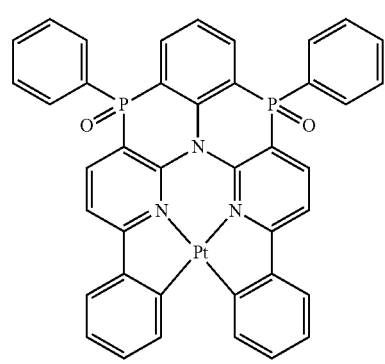
(7)
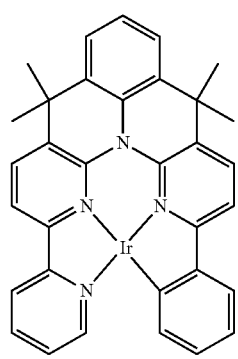
(8)
-continued
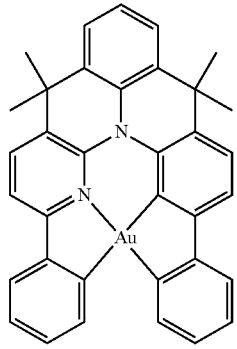
(9)
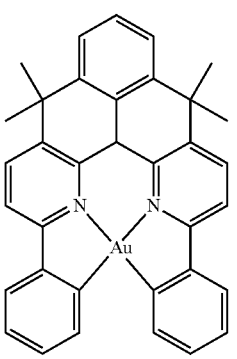
(10)
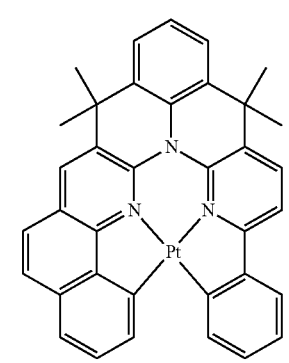
(11)
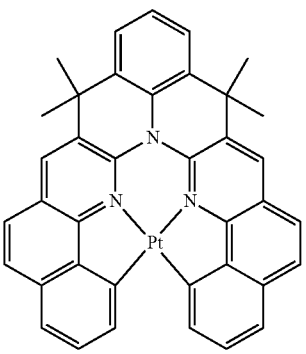
(12)

(13)
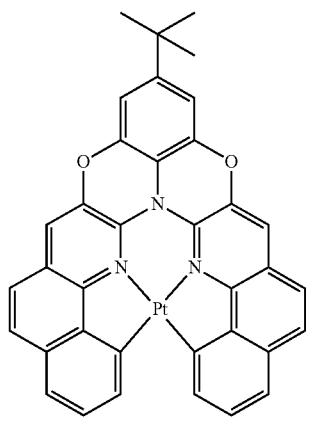
(14)
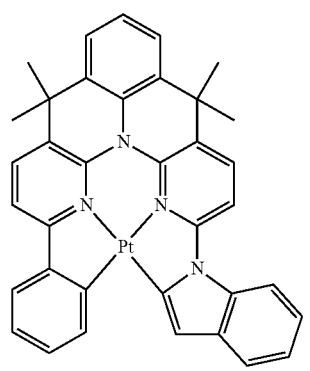
(15)
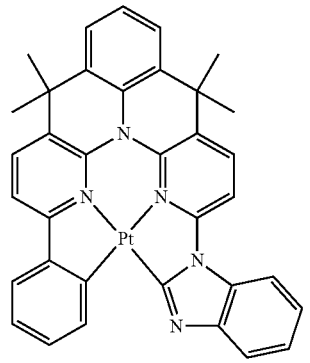
(16)
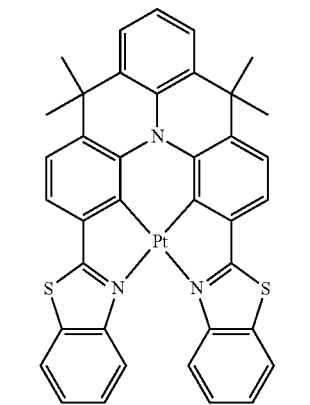
(17)
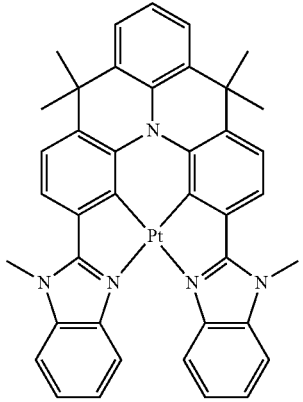
(18)
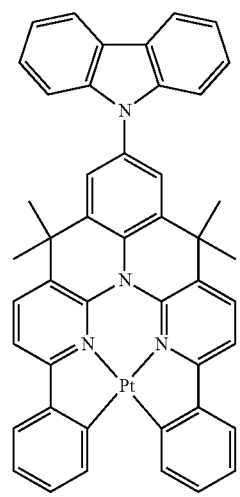
(19)
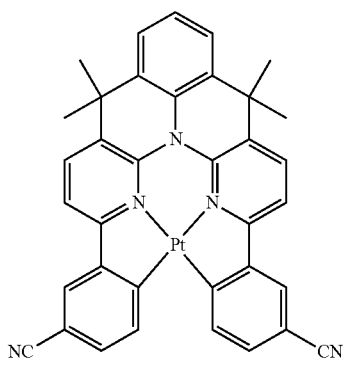
(20)
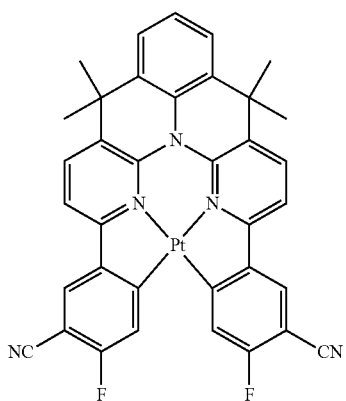

(21)
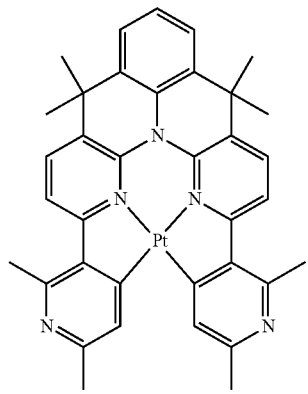

(22)
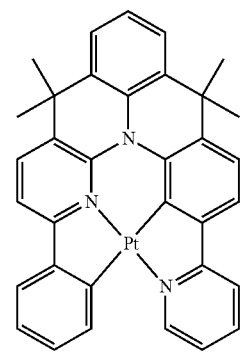

(23)
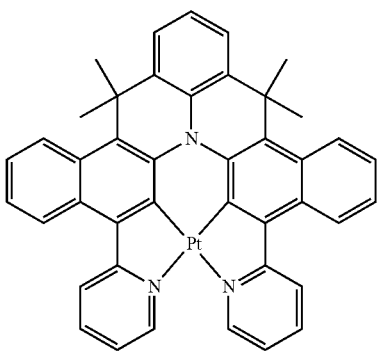

(24)
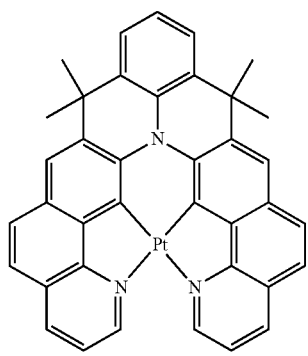

(25)
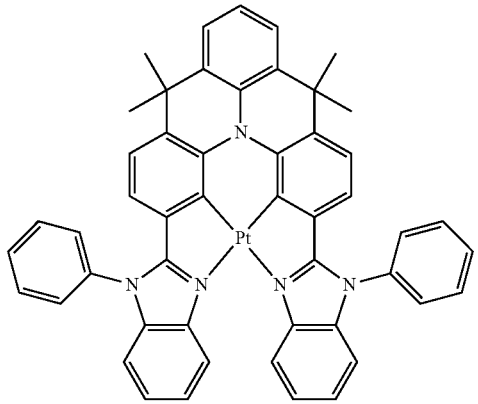

(26)
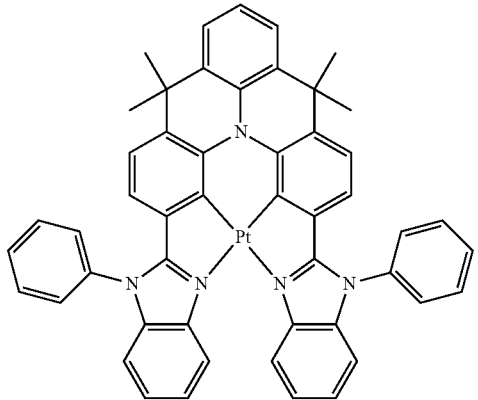

The compounds according to the invention can also be rendered soluble by suitable substitution, for example by relatively long alkyl groups (about 4 to 20 C atoms), in particular branched alkyl groups, or optionally substituted aryl groups, for example, xylyl, mesityl or branched terphenyl or quaterphenyl groups. Compounds of this type are then soluble in common organic solvents, such as, for example, toluene or xylene, at room temperature in sufficient concentration to be able to process the complexes from solution. These soluble compounds are particularly suitable for processing from solution, for example by printing processes.

The present invention therefore furthermore relates to a formulation, in particular a solution, a suspension or a mini-emulsion, comprising at least one compound of the formula (1) and at least one solvent.

The present invention still furthermore relates to a mixture comprising at least one compound of the formula (1) and at least one further compound, in particular a further compound which is suitable as matrix material for the compound of the formula (1).

The complexes of the formula (1) described above or the preferred embodiments indicated above can be used as active component in the electronic device. An electronic device is taken to mean a device which comprises an anode, a cathode and at least one layer, where this layer comprises at least one organic or organometallic compound. The electronic device according to the invention thus comprises an anode, a cathode and at least one layer which comprises at least one compound of the formula (1) given above. Preferred electronic devices here are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs) or organic laser diodes (O-lasers), comprising at least one compound of the formula (1) given above in at least one layer. Particular preference is given to organic electroluminescent devices. Active components are generally the organic or inorganic materials which have been introduced between the anode and cathode, for example charge-injection, charge-transport or charge-blocking materials, but in particular emission materials and matrix materials. The compounds according to the invention exhibit particularly good properties as emission material in organic electroluminescent devices. Organic electroluminescent devices are therefore a preferred embodiment of the invention.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers, charge-generation layers and/or organic or inorganic p/n junctions. Interlayers which have, for example, an exciton-blocking function and/or control the charge balance in the electroluminescent device may likewise be introduced between two emitting layers. However, it should be pointed out that each of these layers does not necessarily have to be present.

The organic electroluminescent device here may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to three-layer systems, where the three layers exhibit blue, green and orange or red emission (for the basic structure see, for example, WO 2005/011013), or systems which have more than three emitting layers. It may also be a hybrid system, where one or more layers fluoresce and one or more other layers phosphoresce.

In a preferred embodiment of the invention, the organic electroluminescent device comprises the compound of the formula (1) or the preferred embodiments indicated above as emitting compound in one or more emitting layers.

If the compound of the formula (1) is employed as emitting compound in an emitting layer, it is preferably employed in combination with one or more matrix materials. The mixture comprising the compound of the formula (1) and the matrix material comprises between 1 and 99% by vol., preferably between 2 and 90% by vol., particularly preferably between 3 and 40% by vol., especially between 5 and 15% by vol., of the compound of the formula (1), based on the mixture as a whole comprising emitter and matrix material. Correspondingly, the mixture comprises between 99.9 and 1% by vol., preferably between 99 and 10% by vol., particularly preferably between 97 and 60% by vol., in particular between 95 and 85% by vol., of the matrix material, based on the mixture as a whole comprising emitter and matrix material.

The matrix material employed can in general be all materials which are known for this purpose in accordance with the prior art. The triplet level of the matrix material is preferably higher than the triplet level of the emitter.

Suitable matrix materials for the compounds according to the invention are ketones, phosphine oxides, sulfoxides and sulfones, for example in accordance with WO 2004/013080, WO 2004/093207, WO 2006/005627 or WO 2010/006680, triarylamines, carbazole derivatives, for example CBP (N,N-biscarbazolylbiphenyl), m-CBP or the carbazole derivatives disclosed in WO 2005/039246, US 2005/0069729, JP 2004/288381, EP 1205527, WO 2008/086851 or US 2009/0134784, indolocarbazole derivatives, for example in accordance with WO 2007/063754 or WO 2008/056746, indenocarbazole derivatives, for example in accordance with WO 2010/136109 or WO 2011/000455, azacarbazoles, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, diazasilole derivatives, for example in accordance with WO 2010/054729, diazaphosphole derivatives, for example in accordance with WO 2010/054730, triazine derivatives, for example in accordance with WO 2010/015306, WO 2007/063754 or WO 2008/056746, zinc complexes, for example in accordance with EP 652273 or WO 2009/062578, dibenzofuran derivatives, for example in accordance with WO 2009/148015, or bridged carbazole derivatives, for example in accordance with US 2009/0136779, WO 2010/050778, WO 2011/042107 or WO 2011/088877.

It may also be preferred to employ a plurality of different matrix materials as a mixture, in particular at least one electron-conducting matrix material and at least one hole-conducting matrix material. A preferred combination is, for example, the use of an aromatic ketone, a triazine derivative or a phosphine oxide derivative with a triarylamine derivative or a carbazole derivative as mixed matrix for the metal complex according to the invention. Preference is likewise given to the use of a mixture of a charge-trans-porting matrix material and an electrically inert matrix material which is not involved or not essentially involved in charge transport, as described, for example, in WO 2010/108579.

It is furthermore preferred to employ a mixture of two or more triplet emitters together with a matrix. The triplet emitter having the shorter-wave emission spectrum serves as co-matrix for the triplet-emitter having the longer-wave emission spectrum. Thus, for example, the complexes of the formula (1) according to the invention can be employed as co-matrix for triplet emitters emitting at longer wavelength, for example for green- or red-emitting triplet emitters.

The compounds according to the invention can also be employed in other functions in the electronic device, for example as hole-transport material in a hole-injection or -transport layer, as charge-generation material or as electron-blocking material. The complexes according to the invention can likewise be employed as matrix material for other phosphorescent metal complexes in an emitting layer.

The cathode preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag, may also be used in addition to the said metals, in which case combinations of the metals, such as, for example, Mg/Ag, Ca/Ag or Ba/Ag, are generally used. It may also be preferred to introduce a thin interlayer of a material having a high dielectric constant between a metallic cathode and the organic semiconductor. Suitable for this purpose are, for example, alkali metal or alkaline-earth metal fluorides, but also the corresponding oxides or carbonates (for example LiF, $Li_2O$, $BaF_2$, MgO, NaF, CsF, $Cs_2CO_3$, etc.). Organic alkali-metal complexes, for example Liq (lithium quinolinate), are likewise suitable for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example $Al/Ni/NiO_x$, $Al/PtO_x$) may also be preferred. For some applications, at least one of the electrodes must be transparent or partially transparent in order either to facilitate irradiation of the organic material (O-SCs) or the coupling-out of light (OLEDs/PLEDs, O-LASERs). Preferred anode materials here are conductive mixed metal oxides. Particular preference is given to indium tin oxide (ITO) or indium zinc oxide (IZO). Preference is furthermore given to conductive, doped organic materials, in particular conductive doped polymers, for example PEDOT, PANI or derivatives of these polymers.

All materials as are used in accordance with the prior art for the layers can generally be used in the further layers, and the person skilled in the art will be able to combine each of these materials with the materials according to the invention in an electronic device without inventive step.

The device is correspondingly structured (depending on the application), provided with contacts and finally hermetically sealed, since the lifetime of such devices is drastically shortened in the presence of water and/or air.

Preference is furthermore given to an organic electroluminescent device, characterised in that one or more layers are coated by means of a sublimation process, in which the materials are vapour-deposited in vacuum sublimation units at an initial pressure of usually less than $10^{-5}$ mbar, preferably less than $10^{-6}$ mbar. It is also possible for the initial pressure to be even lower or even higher, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, offset printing or nozzle printing, but particularly preferably LITI (light induced thermal imaging, thermal transfer printing) or ink-jet printing. Soluble compounds are necessary for this purpose, which are obtained, for example, through suitable substitution.

The organic electroluminescent device may also be produced as a hybrid system by applying one or more layers from solution and applying one or more other layers by vapour deposition. Thus, for example, it is possible to apply an emitting layer comprising a compound of the formula (1) and a matrix material from solution and to apply a hole-blocking layer and/or an electron-transport layer on top by vacuum vapour deposition.

These processes are generally known to the person skilled in the art and can be applied by him without problems to organic electroluminescent devices comprising compounds of the formula (1) or the preferred embodiments indicated above.

The electronic devices according to the invention, in particular organic electroluminescent devices, are distinguished over the prior art by one or more of the following surprising advantages:

1. Organic electroluminescent devices comprising compounds of the formula (1) as emitting materials have a very long lifetime.
2. Organic electroluminescent devices comprising compounds of the formula (1) as emitting materials have excellent efficiency.
3. The metal complexes according to the invention give access to organic electroluminescent devices which phosphoresce in the blue colour region. In particular blue phosphorescence with good efficiencies and lifetimes can only be achieved with great difficulty in accordance with the prior art.
4. The metal complexes according to the invention are synthetically accessible readily and in good yields.

These advantages mentioned above are not accompanied by an impairment of the other electronic properties.

The invention is explained in greater detail by the following examples, without wishing to restrict it thereby. The person skilled in the art will be able to produce further electronic devices on the basis of the descriptions without inventive step and will thus be able to carry out the invention throughout the range claimed.

EXAMPLES

The following syntheses are carried out, unless indicated otherwise, in dried solvents under a protective-gas atmosphere. The metal complexes are additionally handled with exclusion of light. The solvents and reagents can be purchased, for example, from Sigma-ALDRICH or ABCR. The numbers in square brackets for chemical compounds known from the literature refer to the CAS numbers.

A: Synthesis of Synthones S:

1) Bis(6-phenylpyridin-2-yl)amine S1

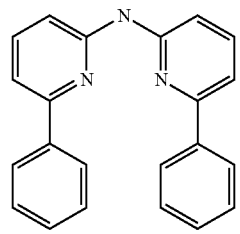 [SMILES: c1ccc(-c2cccc(Nc3cccc(-c4ccccc4)n3)n2)cc1]

1.8 g (6 mmol) of tri-o-tolylphosphine and then 225 mg (1 mmol) of palladium(II) acetate are added with stirring to a mixture of 32.9 g (100 mmol) of bis(6-bromopyridin-2-yl)amine [1195970-59-2], 29.3 g (240 mmol) of phenylboronic acid, 42.4 g (400 mmol) of sodium carbonate, 400 ml of toluene, 200 ml of dioxane and 400 ml of water, and the mixture is heated under reflux for 16 h. After cooling, the organic phase is separated off, washed with 500 ml of water and 500 ml of saturated sodium chloride solution and then dried over sodium sulfate. After removal of the solvent, the residue is recrystallised twice from ethyl acetate/ethanol. Yield: 27.0 g (83 mmol), 83.5%; purity: about 97% according to ¹H-NMR.

The following compounds are prepared analogously:

| Ex. | Boronic acid | Product | Yield |
|---|---|---|---|
| 2 | 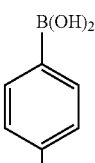 [123324-71-0] | 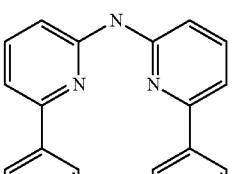 S2 | 80% |
| 3 | 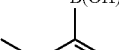 [16419-60-6] | 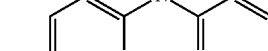 S3 | 78% |
| 4 |  [1765-93-1] | 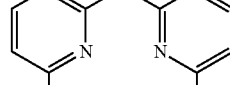 S4 | 73% |
| 5 | 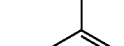 [32316-92-0] | 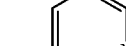 S5 | 56% |

| Ex. | Boronic acid | Product | Yield |
|---|---|---|---|
| 6 | (4-biphenyl)B(OH)₂ | S6 | 81% |
| 7 | (6-tert-butylpyridin-3-yl)B(OH)₂ [1174312-53-8] | S7 | 48% |
| 8 | (benzothiophen-3-yl)B(OH)₂ [113893-08-6] | S8 | 55% |

9) Dimethyl 2-[bis-6-phenylpyridin-2-yl]amino] isophthalate S9

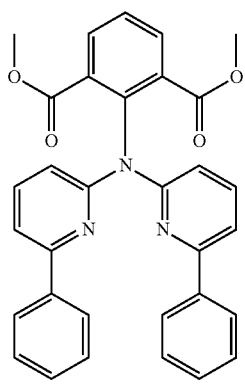 [SMILES: COC(=O)c1cccc(C(=O)OC)c1N(c1cccc(-c2ccccc2)n1)c1cccc(-c2ccccc2)n1]

A mixture of 32.3 g (100 mmol) of S1, 27.3 g (110 mmol) of dimethyl 2-bromoisophthalate [39622-80-5], 20.7 g (150 mmol) of potassium carbonate, 1.3 g (20 mmol) of copper bronze, 150 ml of diphenyl ether and 100 g of glass beads (diameter 5 mm) is heated at 200° C. for 30 h with vigorous stirring. After cooling, the mixture is diluted with 500 ml of toluene, the salts and glass beads are filtered off, and the filtrate is freed from all volatile components in vacuo. The residue is taken up in 500 ml of dichloromethane, the organic phase is washed three times with water and dried over sodium sulfate. The dichloromethane is removed by distillation, during which an equal volume of methanol is added continuously. After switch-over to methanol, this is slowly distilled off until crystallisation commences. After cooling, the solid is filtered off with suction, washed three times with 100 ml of methanol and dried in vacuo. Yield: 40.3 g (78 mmol), 78.1%; purity: about 97% according to ¹H-NMR.

The following compounds are prepared analogously—using the corresponding isophthalic acid esters:

| Ex. | S | Product | Yield |
|---|---|---|---|
| 10 | 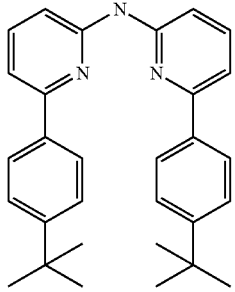 S2 | 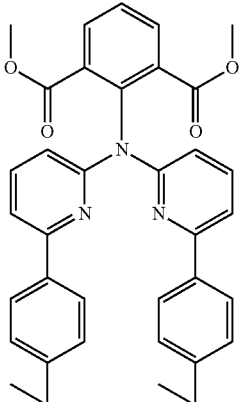 S10 | 66% |
| 11 | 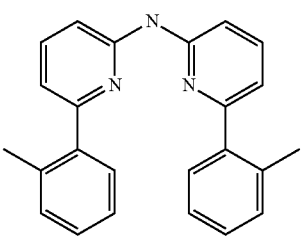 S3 | 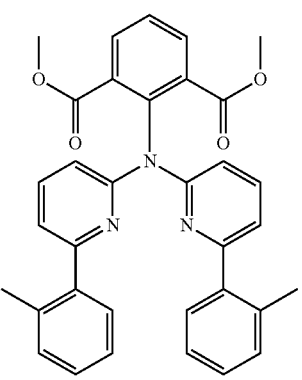 S11 | 58% |
| 12 | 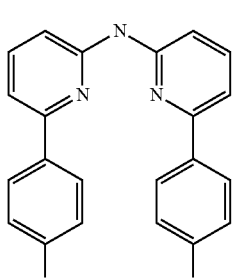 S4 | 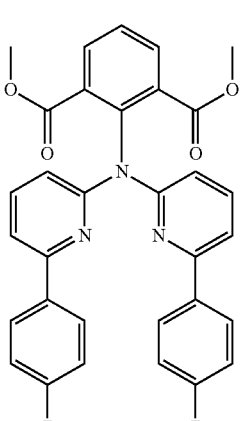 S12 | 70% |

-continued

| Ex. | S | Product | Yield |
|---|---|---|---|
| 13 | S5 | S13 | 68% |
| 14 | S6 | S14 | 71% |
| 15 | S7 | S15 | 54% |

| Ex. | S | Product | Yield |
|---|---|---|---|
| 16 | 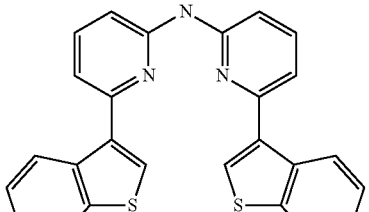 S8 | 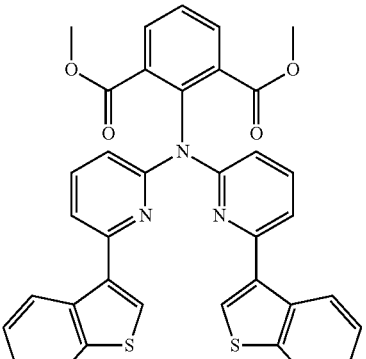 S16 | 57% |
| 17 | 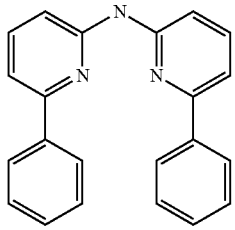 S1 | 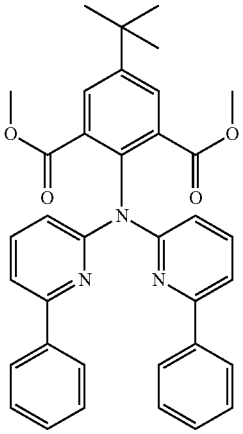 S17 | 74% |

18) 2,12-Diphenyl-1,13,13b-triazanaphtho[3,2,1-de]anthracene-5,9-dione S18

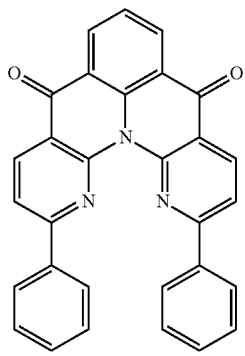 [SMILES: O=c1c2ccc(-c3ccccc3)nc2n2c3nc(-c4ccccc4)ccc3c(=O)c3cccc1c32]

A mixture, warmed to 150° C., of 300 ml of o-dichlorobenzene and 100 ml of conc. sulfuric acid is initially introduced in an apparatus with distillation bridge. A solution of 51.6 g (100 mmol) of S9 in 200 ml of o-dichlorobenzene is added dropwise over the course of 30 min. with vigorous stirring. Stirring is continued until methanol no longer separates out, the mixture allowed to cool, poured into 1000 ml of ice-water, carefully adjusted to pH=10 using NaOH, 1000 ml of dichloromethane are added, the mixture is stirred for a further 30 min., the organic phase is separated off, washed twice with water and dried over sodium sulfate. After removal of the solvents in vacuo, the residue is recrystallised twice from DMF. Yield: 21.5 g (47 mmol), 47.6%; purity: about 97% according to $^1$H-NMR.

The following compounds are prepared analogously:
| Ex. | S | Product | Yield |
|---|---|---|---|
| 19 | S2 | S19 | 51% |
| 20 | S11 | S20 | 37% |
| 21 | S12 | S21 | 44% |
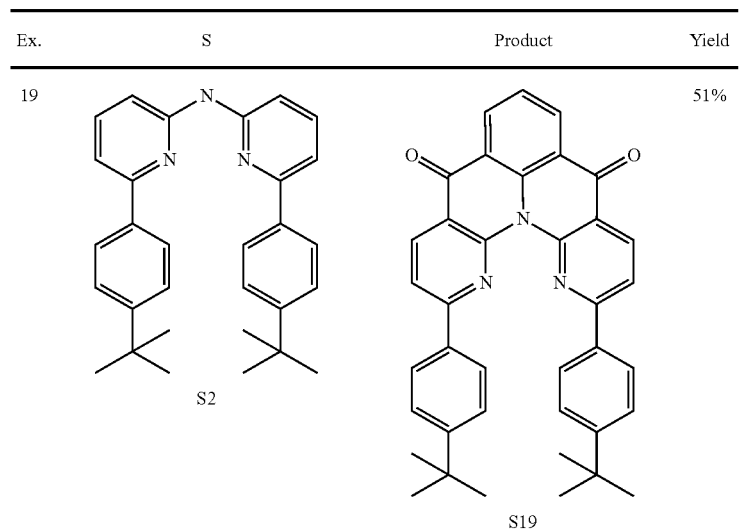
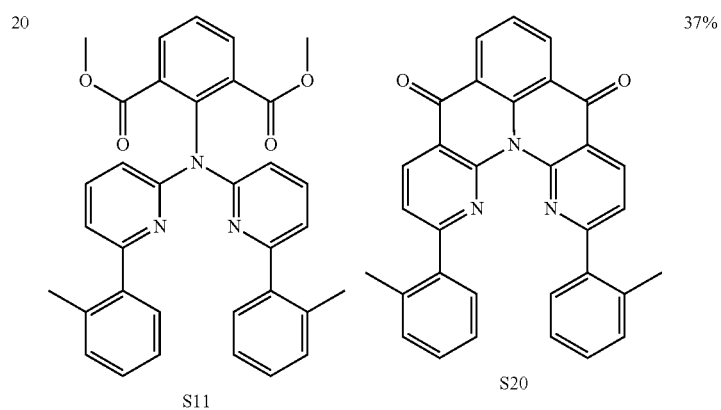
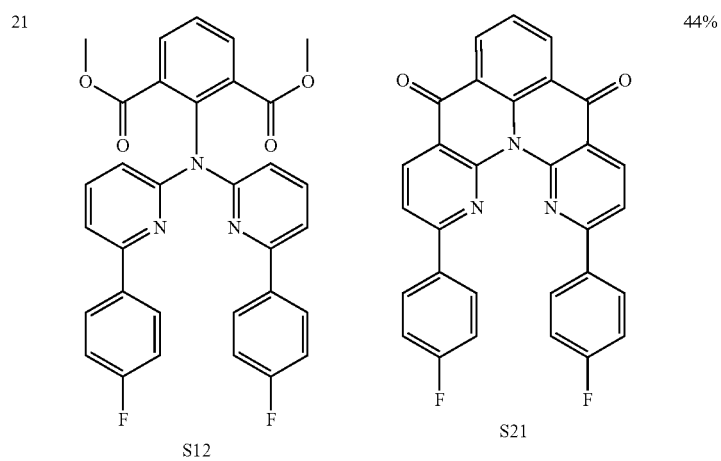

-continued

| Ex. | S | Product | Yield |
|---|---|---|---|
| 22 | S15 | S22 | 23% |
| 23 | S17 | S23 | 48% |

24) Bis-3-bromophenylamine S24

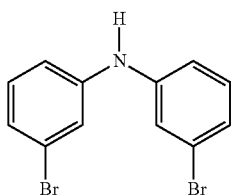 [SMILES: Brc1cccc(Nc2cccc(Br)c2)c1]

A mixture of 235.9 g (200 mmol) of 1,3-dibromobenzene, 50.1 g (50 mmol) of pivaloylamide, 32.6 g (100 mmol) of caesium carbonate, 1.2 g (2 mmol) XanthPhos, 449 mg (2 mmol) of palladium(II) acetate and 500 ml of dioxane is stirred at 100° C. for 8 h. After cooling, the salts are filtered off with suction, rinsed twice with 200 ml of dioxane each time, the organic phase is evaporated to dryness in vacuo, the solid is taken up in 500 ml of ethanol, 50 ml of 5 N HCl are added, and the mixture is heated under reflux for 16 h. The ethanol is removed in vacuo, the residue is taken up in 1000 ml of ethyl acetate, the organic phase is washed once with 300 ml of saturated potassium carbonate solution, three times with 300 ml of water each time and dried over sodium sulfate. The ethyl acetate is removed in vacuo, and the oily residue is brought to crystallisation by addition of about 200 ml of hot methanol. Yield: 13.4 g (41 mmol), 82.0%; purity: about 95% according to $^1$H-NMR.

25) Dimethyl 2-[bis(3-bromophenyl)amino]isophthalate S25

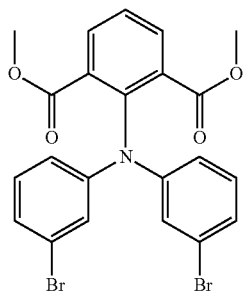 [SMILES: COC(=O)c1cccc(C(=O)OC)c1N(c1cccc(Br)c1)c1cccc(Br)c1]

A mixture of 16.4 g (50 mmol) of S24, 11.7 g (55 mmol) of dimethyl 2-fluoroisophthalate, 6.7 g (60 mmol) of potassium tert-butoxide and 150 ml of anhydrous DMSO is stirred at 80° C. for 24 h. After cooling, the mixture is poured into 1000 ml of ice-water, extracted five times with 200 ml of dichloromethane each time, the dichloromethane is washed three times with 300 ml of water, the organic phase is dried over sodium sulfate, and the dichloromethane is removed in vacuo. The solid is washed by stirring once with a little methanol and dried in vacuo. Yield: 22.3 g (43 mmol), 86.0%; purity: about 95% according to $^1$H-NMR.

26) 2,12-Dibromo-13b-azanaphthyo[3,2,1-de]anthacene-5,9-dione S26

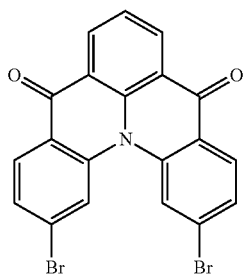 [SMILES: O=c1c2ccc(Br)cc2n2c3cc(Br)ccc3c(=O)c3cccc1c32]

A solution of 26.0 g (50 mmol) of S25 in 300 ml of methanesulfonic acid is slowly heated to 100° C. and stirred for 4 h. After cooling, the mixture is poured into 1000 ml of ice-water, rendered alkaline by addition of NaOH, the precipitated solid is filtered off with suction, washed three times with 100 ml of a mixture of water/EtOH (1:1 vv) each time, three times with 50 ml of EtOH each time and dried in vacuo. The solid obtained in this way is recrystallised from DMF/methanol. Yield: 12.5 g (27 mmol), 54.9%; purity: about 99% according to $^1$H-NMR.

27) 2,12-Dibromo-13b-azanaphthyo[3,2,1-de]anthracene-5,9-bisspiro-9,9'-bifluorene S27

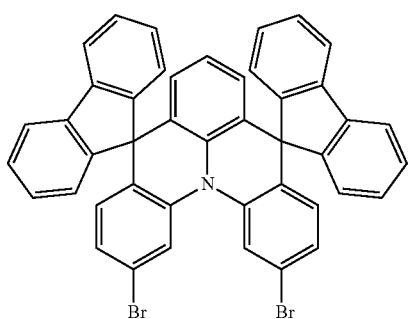 [SMILES: Brc1ccc2c(c1)N1c3cc(Br)ccc3C3(c4ccccc4-c4ccccc43)c3cccc(c31)C21c2ccccc2-c2ccccc21]

Preparation analogous to L7 using 45.5 g (100 mmol) of S26 instead of S18 and carrying out the purification only by recrystallisation. Yield: 37.1 g (52 mmol), 52.0%; purity: about 99% according to $^1$H-NMR

28) 2,12-Dibromo-5,5,9,9-tetramethyl-5H,)H-13b-azanaphthyo[3,2,1-de]-anthracene S28

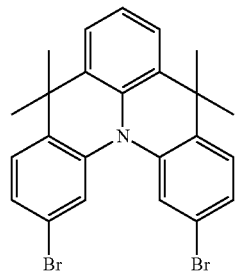 [SMILES: CC1(C)c2ccc(Br)cc2N2c3cc(Br)ccc3C(C)(C)c3cccc1c32]

A suspension of 54.2 g (220 mmol) of anhydrous cerium (III) chloride and 100 g of glass beads (diameter 5 mm) in 300 ml of THF is stirred for 1 h. 51.9 g (100 mmol) of S25 in solid form are then added in portions, and the mixture is again stirred at room temperature for a further 1 h. The suspension is cooled to 0° C., and 600 ml (600 mmol) of a 1 N methylmagnesium chloride in THF is slowly added dropwise at such a rate that the temperature does not exceed 5° C. When the addition is complete, the mixture is allowed to warm to room temperature and is stirred for a further 16 h. The reaction mixture is re-cooled to 0° C., carefully hydrolysed (exothermic!, evolution of gas!) by addition of 1000 ml of 1 N acetic acid, 1000 ml of ethyl acetate are added, the organic phase is separated off, the aqueous phase is extracted three times with 200 ml of ethyl acetate each time, the combined organic phases are washed twice with 300 ml of water, once with 500 ml of saturated sodium chloride solution, dried over sodium sulfate, and the solvent is then removed in vacuo. The residue is taken up in 300 ml of dichloromethane, and the solution is added dropwise to a vigorously stirred mixture, cooled to 0° C., of 500 ml of dichloromethane, 100 g of polyphosphoric acid and 65 ml (1 mol) of methanesulfonic acid. When the addition is complete, the mixture is allowed to warm to room temperature with stirring, stirred for a further 2 h, then poured into 2000 ml of ice-water, the organic phase is separated off, washed three times with 200 ml of water each time, dried over sodium sulfate, and the solvent is then removed in vacuo. The residue is recrystallised twice from DMF. Yield: 33.0 g (68 mmol), 68.3%; purity: about 95% according to $^1$H-NMR.

B: Synthesis of Ligands L:

29) 2,12-Diphenyl-5H,9H-1,13,13b-triazanaphtho[3,2,1-de]anthracene L1

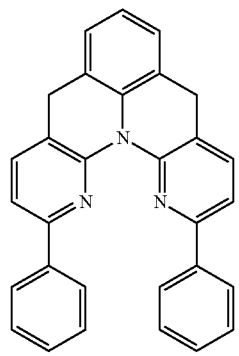 [SMILES: c1ccc(-c2ccc3c(n2)N2c4nc(-c5ccccc5)ccc4Cc4cccc(c42)C3)cc1]

A mixture of 45.2 g (100 mmol) of S18, 9.6 ml (300 mmol) of hydrazine hydrate and 300 ml of triethylene glycol is heated at 180° C. on a water separator for 20 h. After cooling, the mixture is diluted with 100 ml of water, the precipitated solid is filtered off with suction, washed three times with 100 ml of a mixture of water/EtOH (1:1 vv) each time, three times with 100 ml of EtOH and dried in vacuo.

The solid obtained in this way is recrystallised from DMF and subsequently freed from readily volatile and non-volatile components by fractional sublimation (p about $10^{-5}$ mbar, T about 280° C.). Yield: 25.3 g (60 mmol), 59.7%; purity: about 99% according to $^1$H-NMR.

The following compounds are prepared analogously:

| Ex. | S | Product | Yield |
|---|---|---|---|
| 30 | S19 | L2 | 60% |
| 31 | S20 | L3 | 51% |
| 32 | S21 | L4 | 28% |

| Ex. | S | Product | Yield |
|---|---|---|---|
| 33 | S22 | L5 | 64% |
| 34 | S23 | L6 | 58% |

35) 2,12-Diphenyl-5,9-bis-(9,9'-spirobifluorenyl)-1,13,13b-triazanaphtho[3,2,1-de]anthracene L7

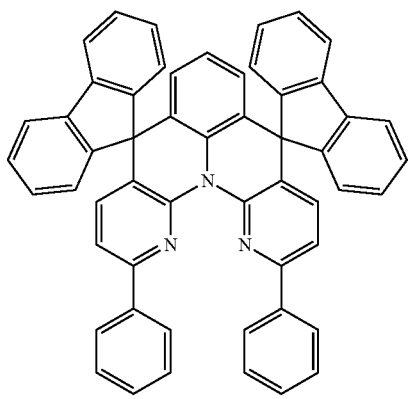 [SMILES: c1ccc(-c2ccc3c(n2)N2c4nc(-c5ccccc5)ccc4C4(c5ccccc5-c5ccccc54)c4cccc(c42)C32c3ccccc3-c3ccccc32)cc1]

The corresponding Grignard reagent is prepared from a mixture of 51.3 g (230 mmol) of 2-bromobiphenyl, 1.6 ml (20 mmol) of 1,2-dichloroethane, 400 ml of THF, 500 ml of toluene and 50 ml of 1,2-dimethoxyethane and 4.9 g (200 mmol) of iodine-activated magnesium turnings. It may be necessary for the mixture to be heated using an oil bath during addition of the bromide solution, or heated under reflux until complete conversion of the magnesium. After the Grignard reagent has been cooled to about 50° C., 45.1 g (100 mmol) of S18 in solid form are added in portions, and the mixture is then stirred at 50° C. for a further 5 h. After cooling, the reaction mixture is evaporated to dryness in vacuo, taken up in 1000 ml of glacial acetic acid, 10 ml of conc. sulfuric acid are added, the mixture is heated under reflux, and 19 ml (200 mmol) of acetic anhydride are then added dropwise. When the addition is complete, the mixture is stirred under reflux for a further 2 h, then allowed to cool with stirring, the precipitated solid is filtered off with suction, washed once with 300 ml of glacial acetic acid and then five times with 100 ml of ethanol each time. The solid obtained in this way is recrystallised from DMF and subsequently freed from readily volatile and non-volatile components by fractional sublimation (p about $10^{-5}$ mbar, T about 280° C.). Yield: 45.9 g (63 mmol), 63.4%; purity: about 99% according to $^1$H-NMR.

The following compounds are prepared analogously:
| Ex. | S | Product | Yield |
|---|---|---|---|
| 36 | 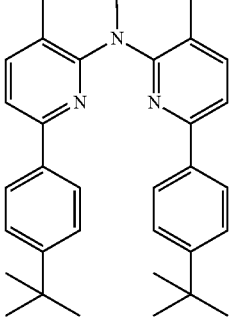<br>S19 | 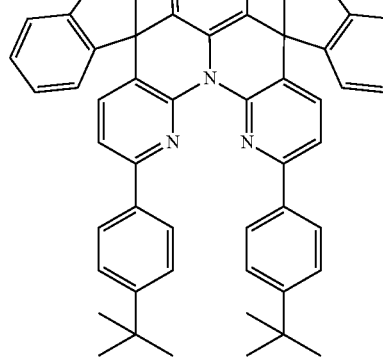<br>L8 | 58% |
| 37 | 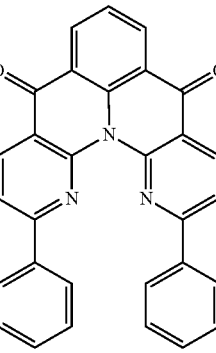<br>S20 | 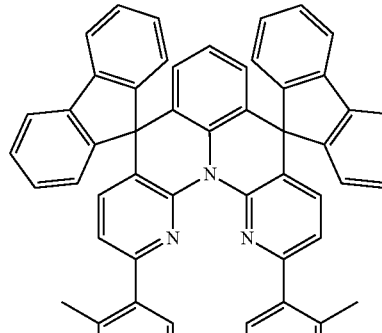<br>L9 | 41% |
| 38 | 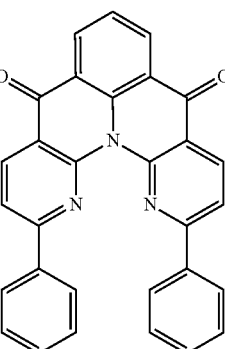<br>S21 | 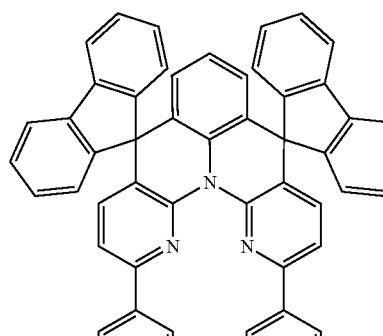<br>L10 | 55% |

| Ex. | S | Product | Yield |
|---|---|---|---|
| 39 | S22 | L11 | 32% |
| 40 | S23 | L12 | 46% |

41) 5,5,9,9-Tetramethyl-2,12-diphenyl-5H,9H-1,13,13b-triazanaphtho[3,2,1-de]anthracene L13

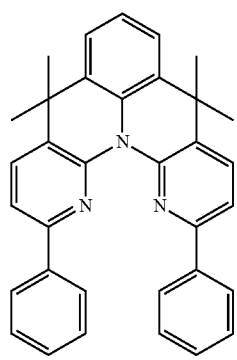 [SMILES: CC1(C)c2ccc(-c3ccccc3)nc2N2c3nc(-c4ccccc4)ccc3C(C)(C)c3cccc1c32]

A suspension of 54.2 g (220 mmol) of anhydrous cerium (III) chloride and 100 g of glass beads (diameter 5 mm) in 400 ml of THF is stirred for 1 h. 51.6 g (100 mmol) of S9 in solid form is then added in portions, and the mixture is again stirred at room temperature for a further 1 h. The suspension is cooled to 0° C., and 600 ml (600 mmol) of a 1 N methylmagnesium chloride in THF are slowly added dropwise at such a rate that the temperature does not exceed 5° C. When the addition is complete, the mixture is allowed to warm to room temperature and is stirred for a further 16 h.

The reaction mixture is re-cooled to 0° C., carefully hydrolysed (exothermic!, evolution of gas!) by addition of 650 ml of 1 N acetic acid, 1000 ml of ethyl acetate are added, the organic phase is separated off, the aqueous phase is extracted three times with 200 ml of ethyl acetate each time, the combined organic phases are washed twice with 300 ml of water and once with 500 ml of saturated sodium chloride solution, dried over sodium sulfate, and the solvent is then removed in vacuo. The residue is taken up in 300 ml of methanesulfonic acid, 100 g of polyphosphoric acid are added, the mixture is slowly heated to 120° C. and stirred for a further 4 h. After cooling, the mixture is poured into 1000 ml of ice-water, rendered alkaline by addition of NaOH, the precipitated solid is filtered off with suction, washed three times with 200 ml of a mixture of water/EtOH (1:1 vv) each time, three times with 100 ml of EtOH and dried in vacuo.

The solid obtained in this way is recrystallised from DMF and subsequently freed from readily volatile and non-volatile components by fractional sublimation (p about 10⁻⁵ mbar, T about 280° C.). Yield: 14.9 g (31 mmol), 31.1%; purity: about 99% according to ¹H-NMR.
The following compounds are obtained analogously:
| Ex. | S | Product | Yield |
|---|---|---|---|
| 42 | 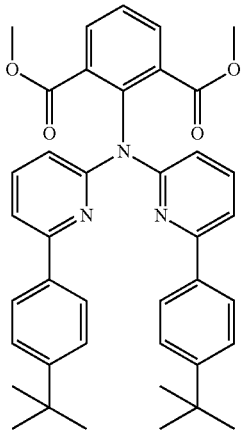 S10 | 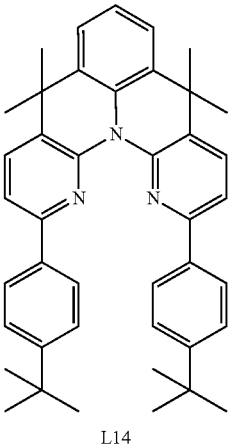 L14 | 33% |
| 43 | 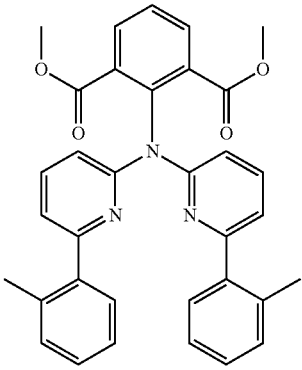 S11 | 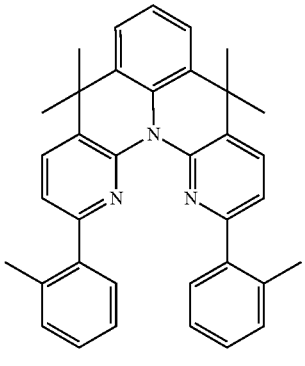 L15 | 27% |
| 44 | 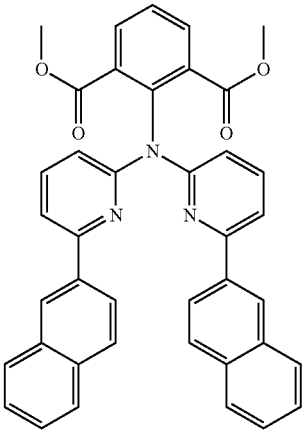 S13 | 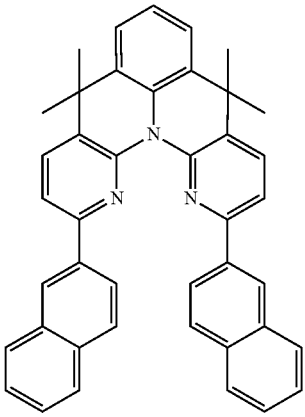 L15 | 24% |

-continued

| Ex. | S | Product | Yield |
|---|---|---|---|
| 45 | S15 | L16 | 35% |
| 46 | S16 | L17 | 13% |
| 47 | S17 | L18 | 30% |

48) 2,12-Dipyridin-2-yl-5H,9H-5,9-bisspiro(9,9'-fluorenyl)-13b-azanaphtho[3,2,1-de]anthracene L19

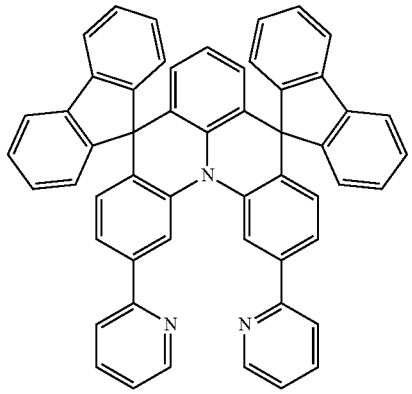 [SMILES: c1ccc(-c2ccc3c(c2)N2c4cc(-c5ccccn5)ccc4C4(c5ccccc5-c5ccccc54)c4cccc(c42)C32c3ccccc3-c3ccccc32)nc1]

A mixture of 36.4 g (50 mmol) of S27, 30.8 g (150 mmol) of 2-(4,4,5,5-tetramethyl-1,3,2-dioxaborolan-2-yl)pyridine [874186-98-8], 32.8 g (100 mmol) of caesium carbonate, 554 mg (1 mmol) of dppf, 224 mg (1 mmol) of palladium (II)acetate, 198 mg (2 mmol) of copper(I) chloride and 300 ml of DMF is heated at 100° C. for 16 h. After cooling, the precipitated salts are filtered off with suction, rinsed with 200 ml of DMF, the DMF is removed in vacuo, the residue is taken up in 500 ml of ethyl acetate, the organic phase is washed three times with 300 ml of water and once with 500 ml of saturated sodium chloride solution, dried over sodium sulfate, and the solvent is then removed in vacuo. The solid obtained in this way is recrystallised from DMF and subsequently freed from readily volatile and non-volatile components by fractional sublimation (p about $10^{-5}$ mbar, T about 280° C.). Yield: 22.3 g (31 mmol), 61.6%; purity: about 99% according to $^1$H-NMR.

The following compounds are prepared analogously:

| Ex. | Boronic acid ester | Product | Yield |
|---|---|---|---|
| 49 | [791819-04-0] | L20 | 76% |
| 50 | [1073353-83-9] | L21 | 68% |

51) 5,5,9,9-Tetramethyl-2,12-dipyridin-2-yl-5H,9H-13b-azanaphtho-[3,2,1-de]anthracene L22

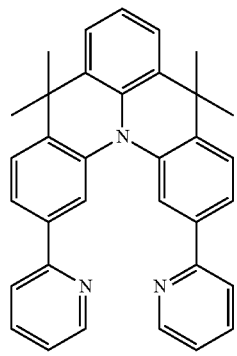 [SMILES: CC1(C)c2ccc(-c3ccccn3)cc2N2c3cc(-c4ccccn4)ccc3C(C)(C)c3cccc1c32]

Procedure analogous to L19, using 24.2 g (50 mmol) of S28 instead of S27. Yield: 17.2 g (36 mmol), 71.7%; purity: about 99% according to $^1$H-NMR.

The following compounds are prepared analogously:

| Ex. | Boronic acid ester | Product | Yield |
|---|---|---|---|
| 52 | [1101205-23-5] | L23 | 63% |
| 53 | [1101205-22-4] | L24 | 70% |

54) 5,5,9,9-Tetramethyl-2,12-dipyridin-2-yl-5H,9H-13b-azanaphtho-[3,2,1-de]anthracene L25

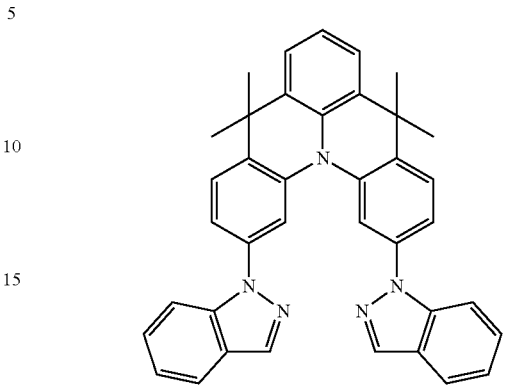

A mixture of 48.3 g (100 mmol) of S28, 29.5 g (250 mmol) of 3aH-indazole [271-38-6], 84.9 g (400 mmol) of tripotassium phosphate, 1.9 g (10 mmol) of copper(I) iodide, 4.6 g (40 mmol) of trans-1,2-diaminocyclohexane, 100 g of glass beads (diameter 5 mm) and 500 ml of toluene is heated under reflux for 20 h. The salts and glass beads are filtered off from the still-warm mixture with suction, rinsed twice with 200 ml of toluene each time, the combined organic phases are washed twice with 500 ml of water each time, once with 500 ml of saturated sodium chloride solution, and the toluene is removed in vacuo. The solid obtained in this way is recrystallised from DMF/ethanol and subsequently freed from readily volatile and non-volatile components by fractional sublimation (p about $10^{-5}$ mbar, T about 290° C.). Yield: 30.7 g (55 mmol), 55.0%; purity: about 99% according to $^1$H-NMR.

The following compound is prepared analogously:

| Ex. | Indazole | Product | Yield |
|---|---|---|---|
| 55 | [3176-62-3] | L26 | 46% |

C: Synthesis of Complexes
Variant A:

A mixture of 10 mmol of potassium tetrachloroplatinate, 10 mmol of ligand L and 50 mmol of lithium acetate (anhydrous) in 100 ml of glacial acetic acid is heated under reflux for 60 h. After dropwise addition of 100 ml of methanol and 100 ml of water to the cooled reaction mixture, the solid is filtered off with suction, washed five times with 25 ml of methanol each time and dried in vacuo. The solid obtained in this way is placed on a Celite bed (aluminium oxide, basic, activity grade 1) with a depth of 3 cm in a hot extractor and then extracted with the extractant indicated (initially introduced amount about 300 ml). When the extraction is complete, the extractant is evaporated to about 100 ml in vacuo. Metal complexes which have excessively good solubility in the extractant are brought to crystallisation by dropwise addition of 200 ml of methanol. The solid of the suspension obtained in this way is filtered off with suction, washed once with about 50 ml of methanol and dried. After drying, the purity of the metal complex is determined by means of NMR and/or HPLC. If the purity is below 99.5%, the hot extraction step is repeated; when a purity of 99.5-99.9% has been reached, the Pt complex is sublimed. The sublimation is carried out in a high vacuum (p about $10^{-6}$ mbar) in the temperature range from about 350 to about 390° C., with the sublimation preferably being carried out in the form of a fractional sublimation.

Variant B:

A mixture of 10 mmol of bis(benzonitrile)platinum(II) dichloride and 10 mmol of ligand L in 50 ml of benzonitrile is heated under reflux for 24 h. After dropwise addition of 100 ml of methanol to the cooled reaction mixture, the solid is filtered off with suction, washed five times with 25 ml of methanol each time and dried in vacuo. Remainder of the work-up as described in the case of variant A.

| Ex. | Ligand L | Pt complex | Variant Extractant | Yield |
|---|---|---|---|---|
| 56 | L1 | PtL1 | A Toluene | 32% |
| 57 | L2 | PtL2 | B Toluene | 28% |
| 58 | L3 | PtL3 | A Toluene | 33% |
| 59 | L4 | PtL4 | A Toluene | 30% |
| 60 | L5 | PtL5 | A Toluene | 21% |
| 61 | L6 | PtL6 | A Toluene | 35% |
| 62 | L7 | PtL7 | A o-Xylene | 25% |
| 63 | L8 | PtL8 | A o-Xylene | 28% |
| 64 | L9 | PtL9 | A o-Xylene | 20% |
| 65 | L10 | PtL10 | A o-Xylene | 27% |
| 66 | L11 | PtL11 | A o-Xylene | 17% |
| 67 | L12 | PtL12 | A o-Xylene | 32% |
| 68 | L13 | PtL13 | A Toluene | 30% |
| 69 | L14 | PtL14 | B Toluene | 30% |
| 70 | L15 | PtL15 | A Toluene | 28% |
| 71 | L16 | PtL16 | A Toluene | 13% |
| 72 | L17 | PtL17 | A Toluene | 24% |
| 73 | L18 | PtL18 | A Toluene | 26% |
| 74 | L19 | PtL19 | A o-Xylene | 34% |
| 75 | L20 | PtL20 | A o-Xylene | 33% |
| 76 | L21 | PtL21 | A o-Xylene | 30% |
| 77 | L22 | PtL22 | A Toluene | 27% |
| 78 | L23 | PtL23 | A Toluene | 25% |
| 79 | L24 | PtL24 | A Toluene | 27% |
| 80 | L25 | PtL25 | A Toluene | 21% |
| 81 | L26 | PtL26 | A Toluene | 19% |

Example

Production of OLEDs

OLEDs according to the invention and OLEDs in accordance with the prior art are produced by a general process in accordance with WO 2004/058911, which is adapted to the circumstances described here (layer-thickness variation, materials used).

The results for various OLEDs are presented in the following examples (see Tables 1 and 2). Glass plates which have been coated with structured ITO (indium tin oxide) in a thickness of 150 nm are coated with 20 nm of PEDOT (poly(3,4-ethylenedioxy-2,5-thiophene), applied by spin-coating from water; purchased from H. C. Starck, Goslar, Germany) for improved processing. These coated glass plates form the substrates to which the OLEDs are applied. The OLEDs have in principle the following layer structure: substrate/optional hole-injection layer (HIL1)/optional hole-injection layer (HIL2)/hole-transport layer (HTL)/electron-blocking layer (EBL)/emission layer (EML)/optional hole-blocking layer (HBL)/electron-transport layer (ETL) and finally a cathode. The cathode is formed by an aluminium layer with a thickness of 100 nm Firstly, vacuum-processed OLEDs are described. For this purpose, all materials are applied by thermal vapour deposition in a vacuum chamber. The emission layer here always consists of at least one matrix material (host material) and an emitting dopant (emitter), which is admixed with the matrix material or matrix materials in a certain proportion by volume by coevaporation. An expression such as M3:M2:Ir(L1)$_3$ (55%:35%:10%) here means that material M3 is present in the layer in a proportion by volume of 55%, M2 is present in the layer in a proportion of 35% and Ir(L1)$_3$ is present in the layer in a proportion of 10%. Analogously, the electron-transport layer may also consist of a mixture of two materials. The precise structure of the OLEDs is shown in Table 1. The materials used for the production of the OLEDs are shown in Table 3.

The OLEDs are characterised by standard methods. For this purpose, the electroluminescence spectra, the current efficiency (measured in cd/A) and the voltage (measured at 1000 cd/m² in V) are determined from current/voltage/luminance characteristic lines (IUL characteristic lines). For selected experiments, the lifetime is determined. The lifetime is defined as the time after which the luminous density has dropped to a certain proportion from a certain initial luminous density. The expression LT50 means that the lifetime given is the time at which the luminous density has dropped to 50% of the initial luminous density, i.e. from, for example, 4000 cd/m² to 2000 cd/m². Depending on the emission colour, different initial luminances were selected. The values for the lifetime can be converted to a figure for other initial luminous densities with the aid of conversion formulae known to the person skilled in the art. The lifetime for an initial luminous density of 1000 cd/m² is a usual figure here.

Use of Compounds According to the Invention as Emitter Materials in Phosphorescent OLEDs The compounds according to the invention can be employed, inter alia, as phosphorescent emitter materials in the emission layer in OLEDs. The compounds Pt(Ref1) and Pt(Ref2) are used as comparison in accordance with the prior art. The results for the OLEDs are summarised in Table 2. In the OLEDs, it is evident here that the materials according to the invention result in efficient blue- to green-emitting OLEDs.

TABLE 1

Structure of the OLEDs

| Ex. | HIL1 Thickness | HIL2 Thickness | HTL Thickness | EML Thickness | HBL Thickness | ETL Thickness |
|---|---|---|---|---|---|---|
| 82 Ref | HIM1 70 nm | HIM2 5 nm | HTM 90 nm | M1:M2:Pt(Ref1) (80%:15%:5%) 40 nm | M1 10 nm | ETM1:LiQ (50%:50%) 30 nm |
| 83 | HIM1 70 nm | HIM2 5 nm | HTM 90 nm | M1:M2:PtL1 (80%:15%:5%) 40 nm | M1 10 nm | ETM1:LiQ (50%:50%) 30 nm |
| 84 | HIM1 70 nm | HIM2 5 nm | HTM 90 nm | M1:M2:PtL2 (80%:15%:5%) 40 nm | M1 10 nm | ETM1:LiQ (50%:50%) 30 nm |
| 85 | HIM1 70 nm | HIM2 5 nm | HTM 90 nm | M1:M2:PtL3 (80%:15%:5%) 40 nm | M1 10 nm | ETM1:LiQ (50%:50%) 30 nm |
| 86 | HIM1 70 nm | HIM2 5 nm | HTM 90 nm | M1:M2:L4 (80%:15%:5%) 40 nm | M1 10 nm | ETM1:LiQ (50%:50%) 30 nm |
| 87 | HIM1 70 nm | HIM2 5 nm | HTM 90 nm | M1:M2:L5 (80%:15%:5%) 40 nm | M1 10 nm | ETM1:LiQ (50%:50%) 30 nm |
| 88 | HIM1 70 nm | HIM2 5 nm | HTM 90 nm | M1:M2:L6 (80%:15%:5%) 40 nm | M1 10 nm | ETM1:LiQ (50%:50%) 30 nm |
| 89 | HIM1 70 nm | HIM2 5 nm | HTM 90 nm | M1:M2:L7 (80%:15%:5%) 40 nm | M1 10 nm | ETM1:LiQ (50%:50%) 30 nm |
| 90 | HIM1 70 nm | HIM2 5 nm | HTM 90 nm | M1:M2:L8 (80%:15%:5%) 40 nm | M1 10 nm | ETM1:LiQ (50%:50%) 30 nm |
| 91 | HIM1 70 nm | HIM2 5 nm | HTM 90 nm | M1:M2:L9 (80%:15%:5%) 40 nm | M1 10 nm | ETM1:LiQ (50%:50%) 30 nm |
| 92 | HIM1 70 nm | HIM2 5 nm | HTM 90 nm | M1:M2:L10 (80%:15%:5%) 40 nm | M1 10 nm | ETM1:LiQ (50%:50%) 30 nm |
| 93 | HIM1 70 nm | HIM2 5 nm | HTM 90 nm | M1:M2:L11 (80%:15%:5%) 40 nm | M1 10 nm | ETM1:LiQ (50%:50%) 30 nm |
| 94 | HIM1 70 nm | HIM2 5 nm | HTM 90 nm | M1:M2:Pt(Ref1)$_3$ (80%:15%:5%) 40 nm | M1 10 nm | ETM1:LiQ (50%:50%) 30 nm |
| 95 | HIM1 70 nm | HIM2 5 nm | HTM 90 nm | M1:M2:L12 (80%:15%:5%) 40 nm | M1 10 nm | ETM1:LiQ (50%:50%) 30 nm |
| 96 | HIM1 70 nm | HIM2 5 nm | HTM 90 nm | M1:M2:L13 (80%:15%:5%) 40 nm | M1 10 nm | ETM1:LiQ (50%:50%) 30 nm |
| 97 | HIM1 70 nm | HIM2 5 nm | HTM 90 nm | M1:M2:L14 (80%:15%:5%) 40 nm | M1 10 nm | ETM1:LiQ (50%:50%) 30 nm |
| 98 | HIM1 70 nm | HIM2 5 nm | HTM 90 nm | M1:M2:L15 (80%:15%:5%) 40 nm | M1 10 nm | ETM1:LiQ (50%:50%) 30 nm |
| 99 | HIM1 70 nm | HIM2 5 nm | HTM 90 nm | M1:M2:L16 (80%:15%:5%) 40 nm | M1 10 nm | ETM1:LiQ (50%:50%) 30 nm |
| 100 | HIM1 70 nm | HIM2 5 nm | HTM 90 nm | M1:M2:L17 (80%:15%:5%) 40 nm | M1 10 nm | ETM1:LiQ (50%:50%) 30 nm |

TABLE 1-continued

Structure of the OLEDs

| Ex. | HIL1 Thickness | HIL2 Thickness | HTL Thickness | EML Thickness | HBL Thickness | ETL Thickness |
|---|---|---|---|---|---|---|
| 101 | HIM1 70 nm | HIM2 5 nm | HTM 90 nm | M1:M2:L18 (80%:15%:5%) 40 nm | M1 10 nm | ETM1:LiQ (50%:50%) 30 nm |
| 102 Ref. | HIM1 80 nm | HIM2 10 nm | HTM 20 nm | M3:Pt(Ref2)$_3$ (93%:7%) 40 nm | ETM1 5 nm | ETM1:LiQ (50%:50%) 25 nm |
| 103 | HIM1 80 nm | HIM2 10 nm | HTM 20 nm | M3:PtL19 (93%:7%) 40 nm | ETM1 5 nm | ETM1:LiQ (50%:50%) 25 nm |
| 104 | HIM1 80 nm | HIM2 10 nm | HTM 20 nm | M3:PtL20 (93%:7%) 40 nm | ETM1 5 nm | ETM1:LiQ (50%:50%) 25 nm |
| 105 | HIM1 80 nm | HIM2 10 nm | HTM 20 nm | M3:PtL21 (93%:7%) 40 nm | ETM1 5 nm | ETM1:LiQ (50%:50%) 25 nm |
| 106 | HIM1 80 nm | HIM2 10 nm | HTM 20 nm | M3:PtL22 (93%:7%) 40 nm | ETM1 5 nm | ETM1:LiQ (50%:50%) 25 nm |
| 107 | HIM1 80 nm | HIM2 10 nm | HTM 20 nm | M3:PtL23 (93%:7%) 40 nm | ETM1 5 nm | ETM1:LiQ (50%:50%) 25 nm |
| 108 | HIM1 80 nm | HIM2 10 nm | HTM 20 nm | M3:PtL24 (93%:7%) 40 nm | ETM1 5 nm | ETM1:LiQ (50%:50%) 25 nm |
| 109 | HIM1 80 nm | HIM2 10 nm | HTM 70 nm | M1:M2:PtL25 (70%:25%:5%) 40 nm | ETM1 5 nm | ETM1:LiQ (70%:30%) 25 nm |
| 110 | HIM1 80 nm | HIM2 10 nm | HTM 70 nm | M1:M2:PtL26 (70%:25%:5%) 40 nm | ETM1 5 nm | ETM1:LiQ (70%:30%) 25 nm |

TABLE 2

Use of compounds according to the invention as emitters in phosphorescent OLEDs

| Ex. | EQE [%] at 1000 cd/m$^2$ | Voltage (V) at 1000 cd/m$^2$ | CIE x/y at 1000 cd/m$^2$ | LT50 (h) at 1000 cd/m$^2$ |
|---|---|---|---|---|
| 82 Ref | 16.5 | 3.8 | 0.35/0.62 | 24000 |
| 83 | 17.6 | 3.7 | 0.35/0.63 | 33000 |
| 84 | 17.8 | 3.8 | 0.35/0.62 | 38000 |
| 85 | 16.9 | 3.6 | 0.35/0.62 | 28000 |
| 86 | 17.6 | 3.8 | 0.23/0.52 | 10000 |
| 87 | 16.8 | 3.9 | 0.21/0.47 | 7000 |
| 88 | 17.6 | 3.6 | 0.35/0.62 | 36000 |
| 89 | 17.0 | 3.7 | 0.35/0.61 | 28000 |
| 90 | 18.0 | 4.1 | 0.35/0.62 | 27000 |
| 91 | 18.2 | 4.3 | 0.35/0.62 | 30000 |
| 92 | 17.7 | 4.1 | 0.34/0.61 | 32000 |
| 93 | 16.0 | 4.2 | 0.23/0.52 | 8000 |
| 94 | 15.7 | 4.5 | 0.23/0.49 | 6000 |
| 95 | 17.8 | 4.6 | 0.35/0.62 | 29000 |
| 96 | 16.9 | 3.8 | 0.35/0.62 | 35000 |
| 97 | 16.7 | 3.7 | 0.35/0.62 | 33000 |
| 98 | 17.0 | 3.6 | 0.47/0.52 | 24000 |
| 99 | 15.5 | 3.5 | 0.23/0.48 | 8000 |
| 100 | 16.0 | 3.9 | 0.54/0.45 | 19000 |
| 101 | 16.9 | 3.9 | 0.35/0.62 | 35000 |
| 102 Ref. | 13.3 | 4.6 | 0.66/0.34 | 29000 |
| 103 | 14.6 | 4.7 | 0.67/0.33 | 35000 |
| 104 | 14.1 | 3.9 | 0.68/0.31 | 30000 |
| 105 | 14.8 | 4.2 | 0.63/0.35 | 24000 |
| 106 | 14.5 | 4.2 | 0.67/0.33 | 34000 |
| 107 | 13.7 | 3.8 | 0.63/0.35 | 8000 |
| 108 | 14.9 | 4.5 | 0.67/0.33 | 34000 |
| 109 | 11.9 | 4.8 | 0.22/0.49 | 5000 |
| 110 | 12.4 | 4.7 | 0.22/0.50 | 7000 |

TABLE 3

Structural formulae of the materials used

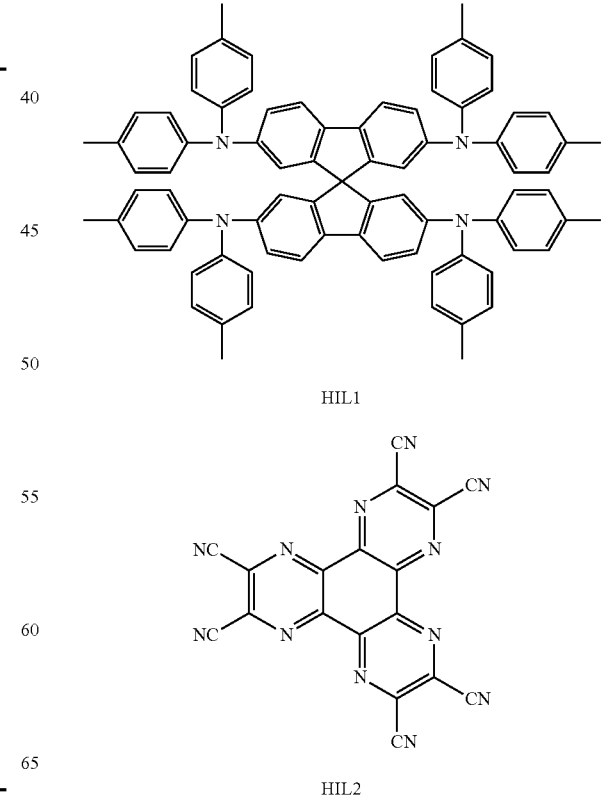

HIL1

HIL2

TABLE 3-continued
Structural formulae of the materials used
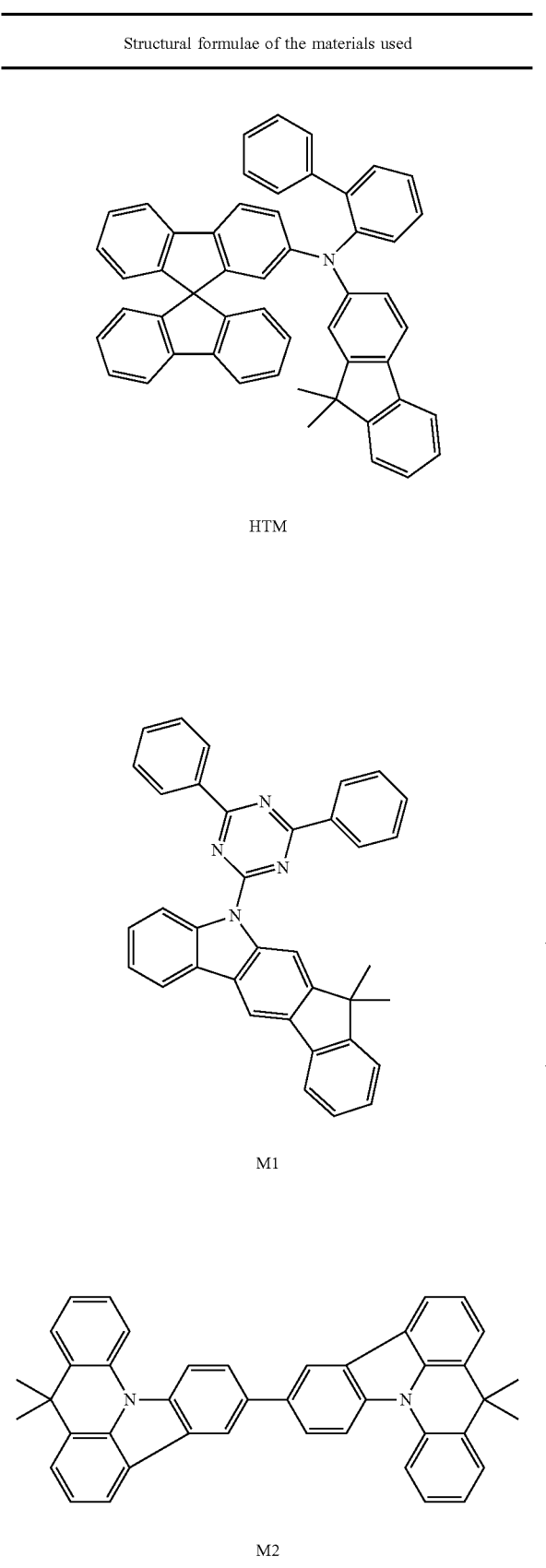
HTM
M1
M2
TABLE 3-continued
Structural formulae of the materials used
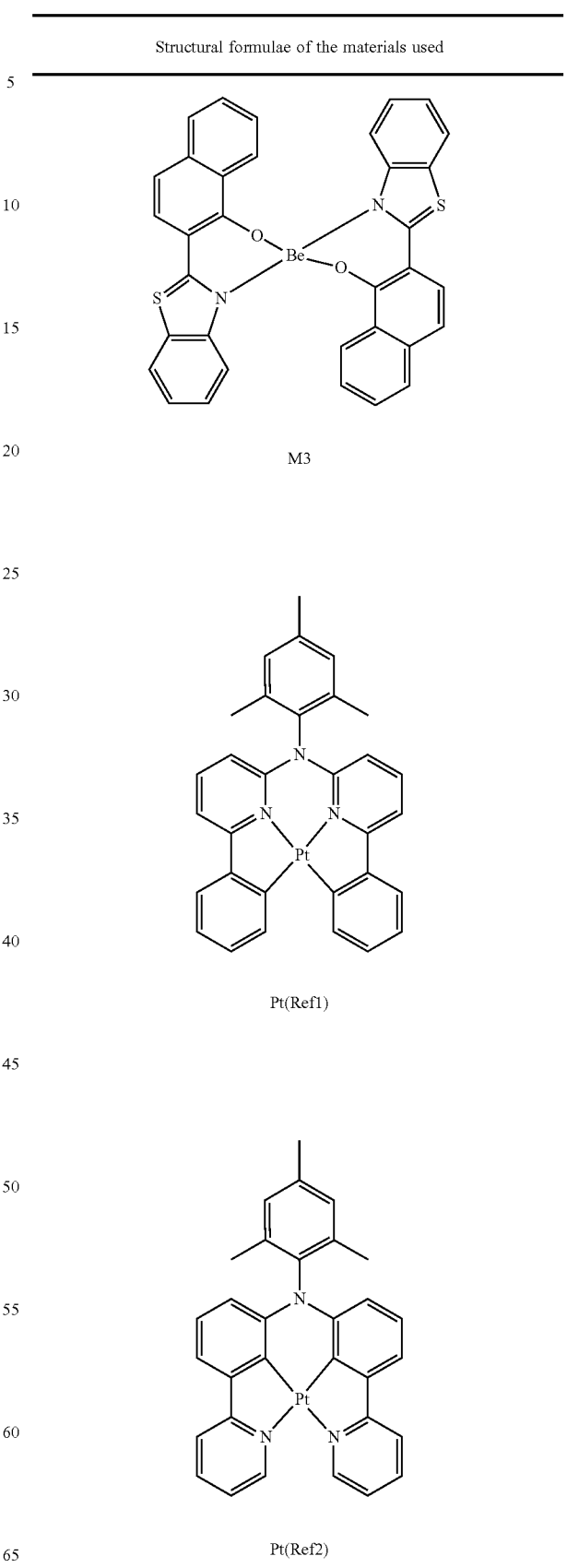
M3
Pt(Ref1)
Pt(Ref2)

TABLE 3-continued

Structural formulae of the materials used

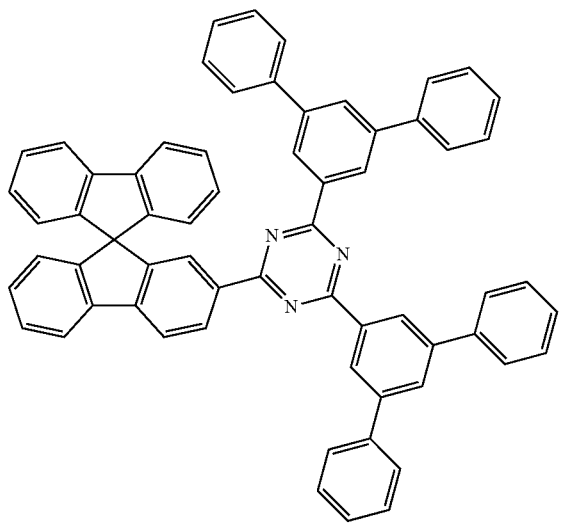 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]

ETM1

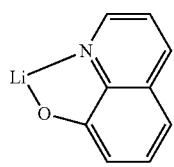

LiQ

Example 111

Synthesis of 2,12-dibromo-13b-azanaphthyro[3,2,1-de]anthracene-5,9-bisspiro-9,9'-dibenzopyran (synthone S29)

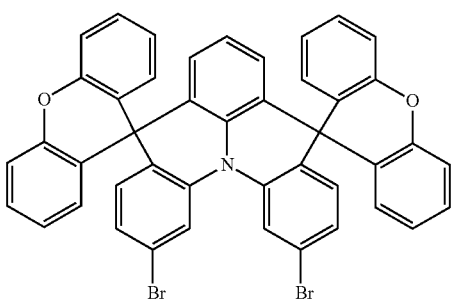 [SMILES: Brc1ccc2c(c1)N1c3cc(Br)ccc3C3(c4ccccc4Oc4ccccc43)c3cccc(c31)C21c2ccccc2Oc2ccccc21]

Preparation analogous to L7, using 57.3 g (230 mmol) of 2-bromophenyl phenyl ether instead of 51.3 g (230 mmol) of 2-bromophenyl and using 45.5 g (100 mmol) of S26 instead of S18, and carrying out the purification only by recrystallisation. Yield: 35.0 g (46 mmol), 46.2%; purity: about 99% according to $^1$H-NMR

Example 112

Synthesis of 2,12-diphenyl-5,9-bis(9,9'-spirodibenzopyranyl)-1,13,13b-triazanaphtho[3,2,1-de]anthracene (Ligand L27)

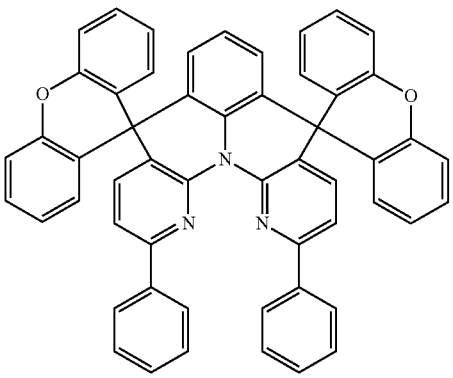 [SMILES: c1ccc(-c2ccc3c(n2)N2c4nc(-c5ccccc5)ccc4C4(c5ccccc5Oc5ccccc54)c4cccc(c42)C32c3ccccc3Oc3ccccc32)cc1]

Procedure analogous to Example 35, using 57.3 g (230 mmol) of 2-bromophenyl phenyl ether instead of 51.3 g (230 mmol) of 2-bromobiphenyl. Yield: 49.9 g (66 mmol), 66.0%; purity: about 99% according to $^1$H-NMR.

Example 113

2,12-Dipyridin-2-yl-5H,9H-5,9-bisspiro(9,9'-fluorenyl)-13b-azanaphtho[3,2,1-de]anthracene (ligand L28)

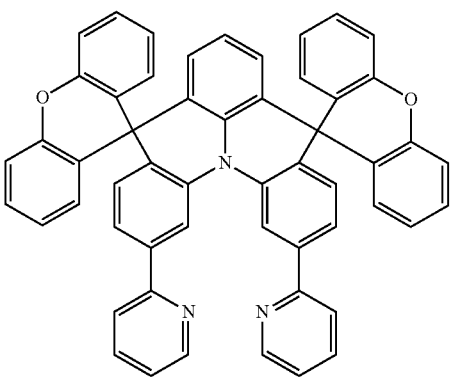 [SMILES: c1ccc(-c2ccc3c(c2)N2c4cc(-c5ccccn5)ccc4C4(c5ccccc5Oc5ccccc54)c4cccc(c42)C32c3ccccc3Oc3ccccc32)nc1]

Procedure analogous to Example 48, using 38.0 g (50 mmol) of S29 instead of 36.4 g (50 mmol) of S27. Yield: 20.5 g (27 mmol), 54.1%; purity: about 99% according to $^1$H-NMR.

Synthesis of the Complexes

The complexes are synthesised by the complexing process mentioned above under C) variant A.

| Ex. | Ligand L | Pt complex | Variant Extractant | Yield |
|---|---|---|---|---|
| 114 | L27 | PtL27 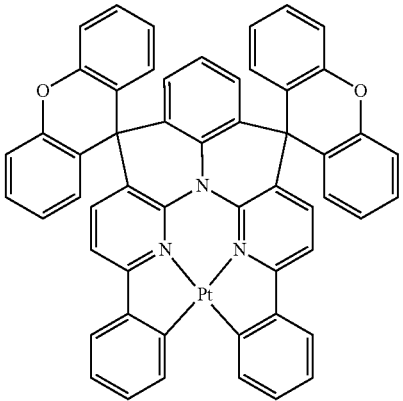 | A Toluene | 29% |
| 115 | L28 | PtL28 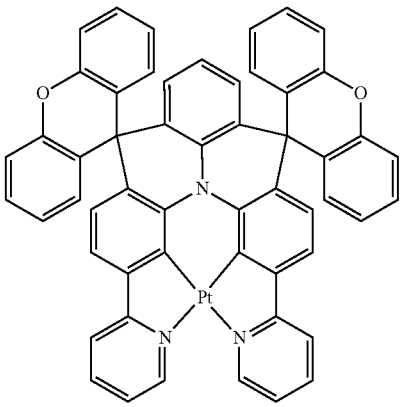 | A Toluene | 31% |
The OLEDs are produced as described above. The OLEDs have the following structure:
| Ex. | HIL1 | HIL1 Thickness | HIL2 Thickness | HTL Thickness | EML Thickness | HBL Thickness | ETL Thickness |
|---|---|---|---|---|---|---|---|
| 116 | HIM1 | 70 nm | HIM2 5 nm | HTM 90 nm | M1:M2:PtL27 (80%:15%:5%) 40 nm | M1 10 nm | ETM1:LiQ (50%:50%) 30 nm |
| 117 | HIM1 | 80 nm | HIM2 10 nm | HTM 20 nm | M3:PtL19 (93%:7%) 40 nm | ETM1 5 nm | ETM1:LiQ (50%:50%) 25 nm |

The following results are obtained with these OLEDs:

| Ex. | EQE [%] at 1000 cd/m2 | Voltage (V) at 1000 cd/m2 | CIE x/y at 1000 cd/m² | LT50 (h) at 1000 cd/m² |
|---|---|---|---|---|
| 116 | 16.9 | 3.9 | 0.34/0.62 | 38000 |
| 117 | 15.2 | 4.4 | 0.67/0.33 | 48000 |

The invention claimed is:
1. A compound of the formula (1),

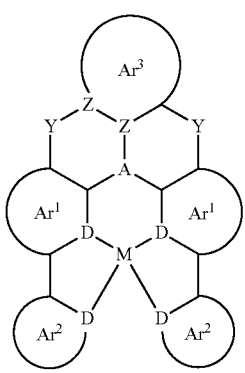

formula (1)

where the following applies to the symbols used:
M is a transition metal;
A is N, P, B, C⁻ or CR;
Y is on each occurrence, identically or differently, $CR_2$, NR, O S or a single bond, where a maximum of one group Y stands for a single bond;
Z is on each occurrence, identically or differently, C or N, with the proviso that both Z stand for C if $Ar^3$ stands for an aromatic or heteroaromatic six-membered ring, and that either both Z stand for C or one Z stands for C and the other Z stands for N if $Ar^3$ stands for a heteroaromatic five-membered ring;
D is on each occurrence, identically or differently, C or N;
$Ar^1$ is on each occurrence, identically or differently, together with the group D and the three carbon atoms explicitly drawn in, one carbon bonded to Y, one carbon bonded to A and one carbon bonded to $Ar^2$, an aryl or heteroaryl group having 5 to 13 aromatic ring atoms, which is optionally substituted by one or more radicals $R^1$;
$Ar^2$ is on each occurrence, identically or differently, together with the group D and the carbon atom explicitly drawn in, and bonded to $Ar^1$, an aryl or heteroaryl group having 5 to 13 aromatic ring atoms, which is optionally substituted by one or more radicals $R^1$;
$Ar^3$ is, together with the two groups Z and the carbon atom, an aryl or heteroaryl group having 5 to 10 aromatic ring atoms, which is optionally substituted by one or more radicals $R^1$;
R and $R^1$ is on each occurrence, identically or differently, H, D, F, Cl, Br, I, $N(R^2)_2$, CN, $NO_2$, OH, COOH, $C(=O)N(R^2)_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which is optionally substituted by one or more radicals $R^2$, where one or more non-adjacent $CH_2$ groups is optionally replaced by $R^2C=CR^2$, C≡C, $Si(R^2)_2$, C=O, $NR^2$, O, S or $CONR^2$ and where one or more H atoms is optionally replaced by D, F, Cl, Br, I or CN, or an aromatic or hetero-aromatic ring system having 5 to 60 aromatic ring atoms, which may in each case be substituted by one or more radicals $R^2$, or an aryloxy or heteroaryloxy group having 5 to 40 aromatic ring atoms, which is optionally substituted by one or more radicals $R^2$, or an aralkyl or heteroaralkyl group having 5 to 40 aromatic ring atoms, which is optionally substituted by one or more radicals $R^2$, or a diarylamino group, diheteroarylamino group or arylheteroarylamino group having 10 to 40 aromatic ring atoms, which is optionally substituted by one or more radicals $R^2$; two adjacent radicals R or two adjacent radicals $R^1$ here may also form a mono- or polycyclic, aliphatic or aromatic ring system with one another; furthermore, the radicals $R^1$ which are bonded to adjacent groups $Ar^1$ and $Ar^2$ may also form a mono- or polycyclic, aliphatic or aromatic ring system with one another;

$R^2$ is on each occurrence, identically or differently, H, D, F, Cl, Br, I, $N(R^3)_2$, CN, $NO_2$, $Si(R^3)_3$, $B(OR^3)_2$, $C(=O)R^3$, $P(=O)(R^3)_2$, $S(=O)R^3$, $S(=O)_2R^3$, $OSO_2R^3$, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which is optionally substituted by one or more radicals $R^3$, where one or more non-adjacent $CH_2$ groups is optionally replaced by $R^3C=CR^3$, C≡C, $Si(R^3)_2$, C=O, $NR^3$, O, S or $CONR^3$ and where one or more H atoms is optionally replaced by D, F, Cl, Br, I, CN or $NO_2$, or an aromatic or heteroaromatic ring system having 5 to 60 aromatic ring atoms, which may in each case be substituted by one or more radicals $R^3$, or an aryloxy or heteroaryloxy group having 5 to 40 aromatic ring atoms, which is optionally substituted by one or more radicals $R^3$, or an aralkyl or heteroaralkyl group having 5 to 40 aromatic ring atoms, which is optionally substituted by one or more radicals $R^3$, or a diarylamino group, diheteroarylamino group or arylheteroarylamino group having 10 to 40 aromatic ring atoms, which is optionally substituted by one or more radicals $R^3$;

$R^3$ is on each occurrence, identically or differently, H, D, F or an aliphatic or aromatic hydrocarbon radical having 1 to 20 C atoms, in which, in addition, one or more H atoms is optionally replaced by F; two or more substituents $R^3$ here may also form a mono- or polycyclic, aliphatic ring system with one another.

2. The compound according to claim 1, wherein M is selected from the group consisting of platinum, palladium, nickel, rhodium, iridium and gold.

3. The compound according to claim 1, wherein two groups D stand for N and the other two groups D stand for C.

4. The compound according to claim 1, wherein Y stands, identically or differently on each occurrence, for $CR_2$ or for a single bond, where a maximum of one group Y stands for a single bond.

5. The compound according to claim 1, wherein the two bridges Y are selected identically.

6. A compound according to claim 1 of the formula (2),

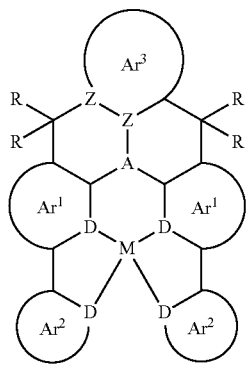

formula (2)

where the symbols used have the meanings given in claim 1.

7. The compound according to claim 1, wherein $Ar^3$ is selected from the structures of the formulae (3), (4) and (5),

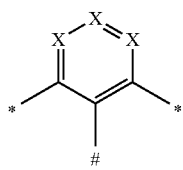

formula (3)

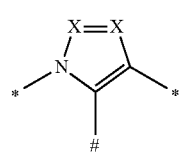

formula (4)

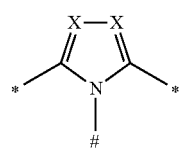

formula (5)

where X stands, identically or differently on each occurrence, for $CR^1$ or N or where two adjacent groups X in formula (3) together stand for NR, O or S and the other group X stands for $CR^1$ or N; * indicates the bond to Y, and # indicates the bond to A.

8. The compound according to claim 1, wherein $Ar^1$ is selected, identically or differently on each occurrence, from the structures of the formulae (6) to (9), (11) and (14),

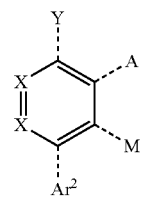

Formula (6)

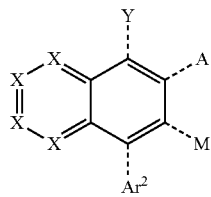

Formula (7)

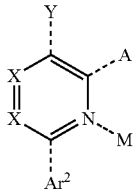

Formula (8)

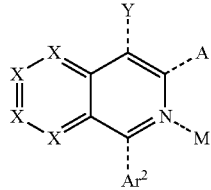

Formula (9)

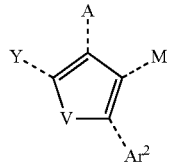

Formula (11)

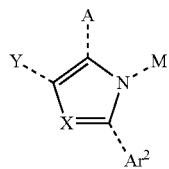

Formula (14)

where the bond to A, Y, M and $Ar^2$ is in each case indicated by the dashed bonds, X stands on each occurrence, identically or differently, for $CR^1$ or N, V stands on each occurrence, identically or differently, for O, S or $NR^1$ and $R^1$ has the same meaning as described in claim 1.

9. The compound according to claim 1, wherein $Ar^2$ is selected, identically or differently on each occurrence, from the structures of the formulae (17)-(24), (27)-(33) and (35)-(38), Formula (17)

Formula (18)

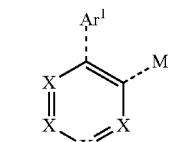

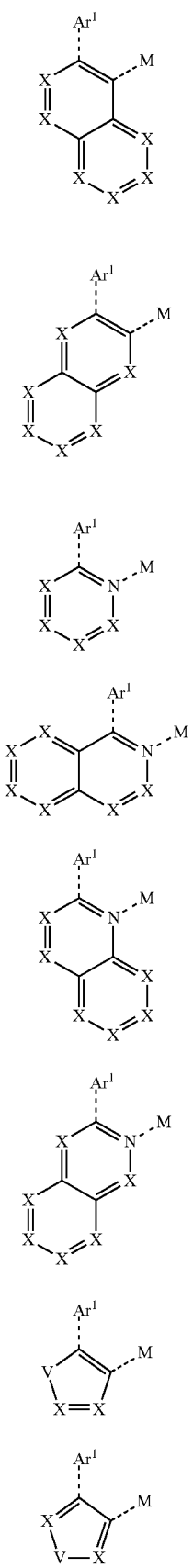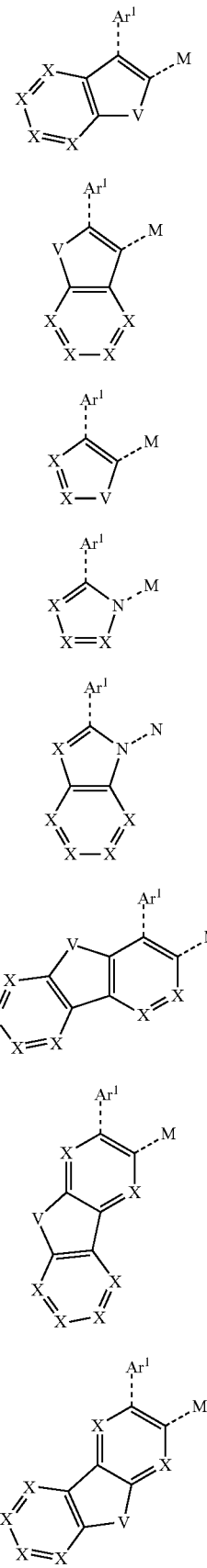

-continued

Formula (38)

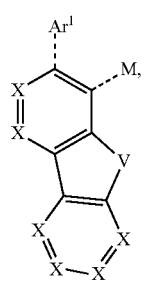

where the bond to M and Ar¹ is in each case indicated by the dashed bonds, X stands on each occurrence, identically or differently, for CR¹ or N, V stands on each occurrence, identically or differently, for O, S or NR¹ and R¹ has the same meaning as described in claim 1.

10. The compound according to claim 1, wherein R¹ is selected on each occurrence, identically or differently, from the group consisting of H, D, F, Br, I, N(R²)₂, CN, Si(R²)₃, B(OR²)₂, C(=O)R², a straight-chain alkyl group having 1 to 10 C atoms or an alkenyl group having 2 to 10 C atoms or a branched or cyclic alkyl group having 3 to 10 C atoms, each of which is optionally substituted by one or more radicals R², where one or more H atoms is optionally replaced by D or F, or an aromatic or heteroaromatic ring system having 5 to 30 aromatic ring atoms, which may in each case be substituted by one or more radicals R²; two adjacent radicals R¹ or two radicals R¹ on adjacent groups Ar¹ and Ar² here may also form a mono- or polycyclic, aliphatic ring system with one another.

11. The compound according to claim 1, wherein, if Y stands for NR, R stands, identically or differently on each occurrence, for an aromatic or heteroaromatic ring system having 5 to 18 aromatic ring atoms, which may in each case be substituted by one or more radicals R², and in that, if Y stands for CR₂, R stands, identically or differently on each occurrence, for H, D, a straight-chain alkyl group having 1 to 10 C atoms or an alkenyl or alkynyl group having 2 to 10 C atoms or a branched or cyclic alkyl group having 3 to 10 C atoms, each of which is optionally substituted by one or more radicals R², where one or more H atoms is optionally replaced by D or F, or an aromatic or heteroaromatic ring system having 5 to 18 aromatic ring atoms, which may in each case be substituted by one or more radicals R²; two or more radicals R which are bonded to the same carbon atom here may also form a mono- or polycyclic, aliphatic or aromatic ring system with one another.

12. A process for the preparation of the compound according to claim 1 which comprises reacting the free ligand with a metal compound.

13. A formulation comprising:
a) at least one compound according to claim 1 and at least one solvent, or
b) a mixture comprising at least one compound according to claim 1 and at least one further compound.

14. The formulation as claimed in claim 13, wherein the formulation is a solution, a suspension or a mini-emulsion.

15. An electronic device which comprises the compound according to claim 1.

16. The electronic device as claimed in claim 15, wherein the device is an organic electroluminescent device, an organic integrated circuit, an organic field-effect transistor, an organic thin-film transistor, an organic light-emitting transistor, an organic solar cell, an organic optical detector, an organic photoreceptor, an organic field-quench device, a light-emitting electrochemical cell or an organic laser diode.

17. An organic electroluminescent device which comprises the compound according to claim 1 employed as emitting compound in one or more emitting layers.

18. An organic electroluminescent device which comprises the compound according to claim 1 employed as emitting compound in one or more emitting layers in combination with one or more matrix materials.

19. The compound according to claim 1, wherein
M is selected from the group consisting of Pt(II), Pd(II), Ni(II), Rh(I), Ir(I) and Au(III);
D is on each occurrence, identically or differently, C or N, where two groups D stand for N and the other two groups D stand for C;
Ar³ is selected from the structures of the formulae (3), (4) or (5)

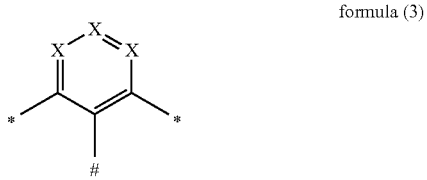

formula (3)

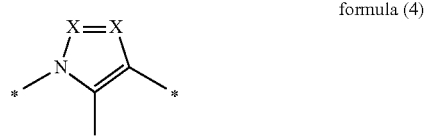

formula (4)

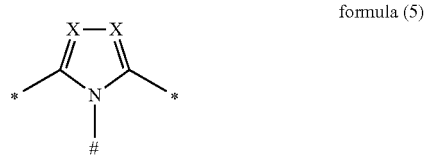

formula (5)

where X stands, identically or differently on each occurrence, for CR¹ or N or where two adjacent groups X in formula (3) together stand for NR, O or S and the other group X stands for CR¹ or N; * indicates the bond to Y, and # indicates the bond to A;
Ar¹ is selected from the structures of the formulae (6) to (9), (11) and (14),

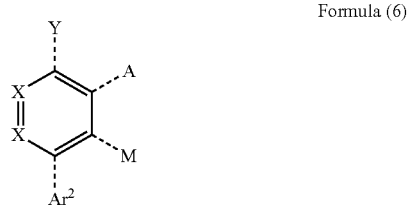

Formula (6)

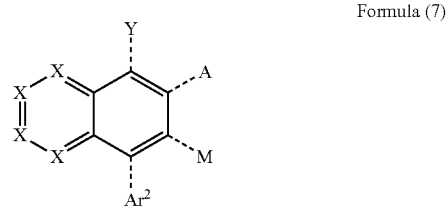

Formula (7)

-continued

Formula (8)
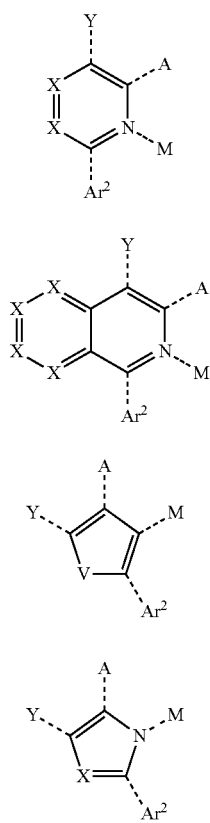

Formula (9)

Formula (11)

Formula (14)

where the bond to A, Y, M and $Ar^2$ is in each case indicated by the dashed bonds, X stands on each occurrence, identically or differently, for $CR^1$ or N, V stands on each occurrence, identically or differently, for O, S or $NR^1$;

$Ar^2$ is selected from the structures of the formulae (17) to (24), (27)-(33) and (35)-(38)

Formula (17)

Formula (18)

Formula (19)

-continued

Formula (20)
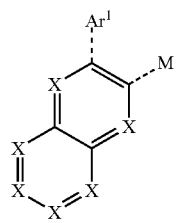

Formula (21)
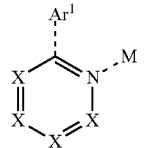

Formula (22)
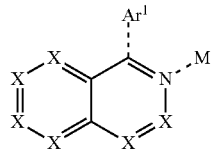

Formula (23)
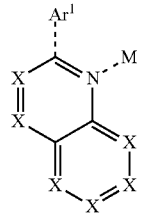

Formula (24)
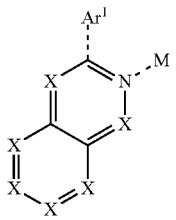

Formula (27)
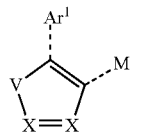

Formula (28)
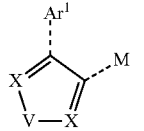

Formula (29)
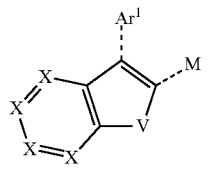

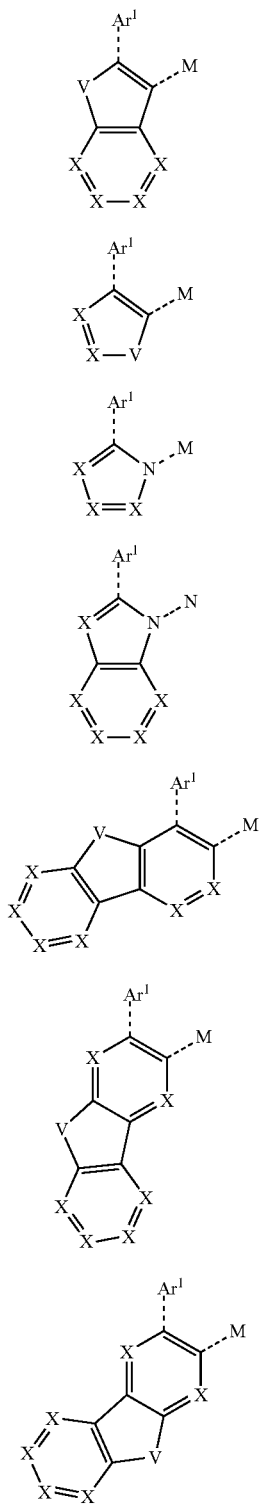

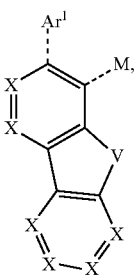

where the bond to M and Ar¹ is in each case indicated by the dashed bonds, X stands on each occurrence, identically or differently, for $CR^1$ or N, V stands on each occurrence, identically or differently, for O, S or $NR^1$;

$R^1$ is selected on each occurrence, identically or differently, from the group consisting of H, D, F, Br, I, $N(R^2)_2$, CN, $Si(R^2)_3$, $B(OR^2)_2$, $C(=O)R^2$, a straight-chain alkyl group having 1 to 10 C atoms or an alkenyl group having 2 to 10 C atoms or a branched or cyclic alkyl group having 3 to 10 C atoms, each of which is optionally substituted by one or more radicals $R^2$, where one or more H atoms is optionally replaced by D or F, or an aromatic or heteroaromatic ring system having 5 to 30 aromatic ring atoms, which may in each case be substituted by one or more radicals $R^2$; two adjacent radicals $R^1$ or two radicals $R^1$ on adjacent groups Ar¹ and Ar² here may also form a mono- or polycyclic, aliphatic ring system with one another;

R is, for Y=NR, identically or differently on each occurrence, an aromatic or heteroaromatic ring system having 5 to 18 aromatic ring atoms, which may in each case be substituted by one or more radicals $R^2$; and is, for $Y=CR_2$, identically or differently, H, D, a straight-chain alkyl group having 1 to 10 C atoms or an alkenyl or alkynyl group having 2 to 10 C atoms or a branched or cyclic alkyl group having 3 to 10 C atoms, each of which is optionally substituted by one or more radicals $R^2$, where one or more H atoms is optionally replaced by D or F, or an aromatic or heteroaromatic ring system having 5 to 18 aromatic ring atoms, which may in each case be substituted by one or more radicals $R^2$; or two or more radicals R which are bonded to the same carbon atom here may also form a mono- or polycyclic, aliphatic or aromatic ring system with one another.

20. The compound according to claim 1, wherein M=Pt and A=N.

* * * * *